US011680253B2

(12) United States Patent
Chang et al.

(10) Patent No.: US 11,680,253 B2
(45) Date of Patent: Jun. 20, 2023

(54) TRANSPOSASE-MEDIATED IMAGING OF THE ACCESSIBLE GENOME

(71) Applicant: The Board of Trustees of the Leland Stanford Junior University, Stanford, CA (US)

(72) Inventors: Howard Y. Chang, Palo Alto, CA (US); William J. Greenleaf, Stanford, CA (US); Xingqi Chen, Palo Alto, CA (US); Jason Buenrostro, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 293 days.

(21) Appl. No.: 16/081,381

(22) PCT Filed: Mar. 9, 2017

(86) PCT No.: PCT/US2017/021677
§ 371 (c)(1),
(2) Date: Aug. 30, 2018

(87) PCT Pub. No.: WO2017/156336
PCT Pub. Date: Sep. 14, 2017

(65) Prior Publication Data
US 2019/0071656 A1    Mar. 7, 2019

Related U.S. Application Data

(60) Provisional application No. 62/306,504, filed on Mar. 10, 2016.

(51) Int. Cl.
| | |
|---|---|
| C07K 19/00 | (2006.01) |
| C12N 9/22 | (2006.01) |
| C12Q 1/6806 | (2018.01) |
| C12N 15/90 | (2006.01) |
| C07K 1/13 | (2006.01) |

(52) U.S. Cl.
CPC .............. C12N 9/22 (2013.01); C07K 1/13 (2013.01); C12N 15/90 (2013.01); C12Q 1/6806 (2013.01); *C07K 2319/60* (2013.01)

(58) Field of Classification Search
CPC ........ C12N 9/22; C07K 1/13; C07K 2319/60; C12Q 1/6806
See application file for complete search history.

(56) References Cited

U.S. PATENT DOCUMENTS

| | | | |
|---|---|---|---|
| 7,135,296 B2 | 11/2006 | Baranov et al. | |
| 7,316,903 B2 | 1/2008 | Yanagihara et al. | |
| 7,479,630 B2 | 1/2009 | Bandura et al. | |
| 2006/0040382 A1 | 2/2006 | Heffron et al. | |
| 2008/0046194 A1 | 2/2008 | Antonov et al. | |
| 2010/0120098 A1* | 5/2010 | Grunenwald | C12Q 1/6855 435/91.2 |
| 2013/0203605 A1 | 8/2013 | Shendure et al. | |
| 2015/0291942 A1* | 10/2015 | Gloeckner | C12N 15/1068 506/2 |
| 2016/0060691 A1* | 3/2016 | Giresi | C12Q 1/6869 506/2 |
| 2016/0209319 A1* | 7/2016 | Adalsteinsson | G06K 9/4652 |

FOREIGN PATENT DOCUMENTS

| | | | | |
|---|---|---|---|---|
| CN | 1230226 A | 9/1999 | | |
| WO | WO 2012/061832 | 5/2012 | | |
| WO | WO-2015179706 A1 * | 11/2015 | ......... | C12N 15/1082 |
| WO | WO-2017034970 A1 * | 3/2017 | ......... | G01N 33/6878 |
| WO | WO-2017075294 A1 * | 5/2017 | ........... | C12Q 1/6886 |

OTHER PUBLICATIONS

Buenrostro et al., 2013, "Transposition of native chromatin for fast and sensitive epigenomic profiling of open chromatin, DNA-binding proteins and nucleosome position," (Nature Methods 10, 1213-1218). (Year: 2013).*
Gloeckner et al Score report for instant SEQ No. 1 (for US 2015/0291942 published Oct. 2015). (Year: 2015).*
Gloeckner et al Score report for instant SEQ No. 2 (for US 2015/0291942 published Oct. 2015). (Year: 2015).*
Gloeckner et al Score report for instant SEQ No. 3 (for US 2015/0291942 published Oct. 2015). (Year: 2015).*
Buenrostro et al ("ATAC-seq: A Method for Assaying Chromatin Accessibility Genome-Wide" Curr Protoc Mol Biol; vol. 109: pp. 1-10, published Jan. 5, 2016). (Year: 2016).*
Chen et al., "ATAC-see reveals the 1-15 accessible genome by transposase-mediated imaging and sequencing". Nature Methods. 2016; 13(12): 1013-1020.

(Continued)

*Primary Examiner* — Catherine S Hibbert
(74) *Attorney, Agent, or Firm* — Casimir Jones, S.C.; Tanya A. Arenson

(57) ABSTRACT

Methods for labeling and imaging the accessible genome using a transposase are disclosed. In some embodiments, a bifunctional transposase complex or transposome is used to insert adaptors comprising chemical tags selectively at accessible sites in the genome where active regulatory DNA is located. Various chemical tags can be used for labeling DNA at insertion sites, including, for example, fluorescent dyes for fluorescence imaging, metal particles for electron microscopy or magnetic manipulation of DNA, isotopic labels, or biotin or other ligands, haptens, substrates, or inhibitors that are recognized by streptavidin, antibodies, enzymes, or receptors. Labeling DNA in this manner can be used to provide spatial information regarding the positioning of regulatory DNA in the genome and makes possible the imaging and sorting of cells based on the status of their regulatory DNA.

20 Claims, 9 Drawing Sheets

Specification includes a Sequence Listing.

(56) References Cited

OTHER PUBLICATIONS

Sos et al., "Characterization 1-15 of chromatin accessibility with a transposome hypersensitive sites sequencing (THS-seq) assay". Genome Biology. 2016; 17(20): 1-15.
Buenrostro et al., "ATAC-seq: A Method for Assaying Chromatin Accessibility Genome-Wide", Curr Protoc Mol Biol., 2016, 109:21.29.1-21.29.9. doi:10.1002/0471142727.mb2129s109.
International Search Report and Written Opinion for PCT/US2017/0211677. dated May 25, 2017. 14 pages.
Extended European Search Report for PCT/US2017021677. dated Jul. 17, 2019. 6 pages.
Extended European Search Report for 21153694.1. dated Jul. 27, 2021. 10 pages.
Office Action for CN App. No. 201780021788.6. dated Aug. 26, 2022. 6 pages.
Adey et al, Rapid, low-input, low-biasRapid, low-input, low-bias construction of shotgun fragment libraries by high-density in vitro transposition. Genome Biol. 2010;11(12):R119.
Aleem et al., Cdc2-cyclin E complexes regulate the G1/S phase transition. Nat Cell Biol. Aug. 2005;7(8):831-6.
Amendola et al., Nuclear lamins are not required for lamina-associated domain organization in mouse embryonic stem cells. EMBO Rep. May 2015;16(5):610-7.
Amini et al., Haplotype-resolved whole genome sequencing by contiguity preserving transposition and combinatorial indexing. Nat Genet. 2014; 46(12): 1343-1349.
Bandura et al., Mass cytometry: technique for real time single cell multitarget immunoassay based on inductively coupled plasma time-of-flight mass spectrometry. Anal Chem. Aug. 15, 2009;81(16):6813-22.
Bickmore et al., Genome architecture: domain organization of interphase chromosomes. Cell. Mar. 14, 2013;152(6):1270-84.
Brinkmann et al., Neutrophil Extracellular Traps Kill Bacteria. Science. 2004; 303: 1532-1535.
Buenrostro et al., Single-cell chromatin accessibility reveals principles of regulatory variation. Nature. Jul. 23, 2015;523(7561):486-90.
Buenrostro et al., Transposition of native chromatin for fast and sensitive epigenomic profiling of open chromatin, DNA-binding proteins and nucleosome position. Nat Methods. Dec. 2013;10(12):1213-8.

Caruccio et al., Preparation of next-generation sequencing libraries using Nextera™ technology: simultaneous DNA fragmentation and adaptor tagging by in vitro transposition. Methods Mol Biol. 2011;733:241-55.
Christophorou et al., Citrullination regulates pluripotency and histone H1 binding to chromatin. Nature. Mar. 6, 2014;507(7490):104-8.
Cusanovich et al., Multiplex single-cell profiling of chromatin accessibility by combinatorial cellular indexing. Science. 2015; 348(6237): 910-914.
Gibcus et al., The hierarchy of the 3D genome. Mol Cell. Mar. 7, 2013;49(5):773-82.
Hinde et al., Changes in chromatin compaction during the cell cycle revealed by micrometer-scale measurement of molecular flow in the nucleus. Biophys J. Feb. 8, 2012;102(3):691-7.
Kolaczkowska et al., Neutrophil recruitment and function in health and inflammation. Nat Rev Immunol. Mar. 2013;13(3):159-75.
Lanctot et al., Dynamic genome architecture in the nuclear space: regulation of gene expression in three dimensions. Nat Rev Genet. Feb. 2007;8(2):104-15.
Lewis et al., Inhibition of PAD4 activity is sufficient to disrupt mouse and human NET formation. Nat Chem Biol. Mar. 2015;11(3):189-91.
Li et al., PAD4 is essential for antibacterial innate immunity mediated by neutrophil extracellular traps. J Exp Med. Aug. 30, 2010;207(9):1853-62.
Lieberman-Aiden et al., Comprehensive mapping of long-range interactions reveals folding principles of the human genome. Science. Oct. 9, 2009;326(5950):289-93.
Picelli et al., Tn5 transposase and tagmentation procedures for massively scaled sequencing projects. Genome Res. Dec. 2014;24(12):2033-40.
Solovei et al., Nuclear architecture of rod photoreceptor cells adapts to vision in mammalian evolution. Cell. Apr. 17, 2009;137(2):356-68.
Tanner et al., Flow cytometer with mass spectrometer detection for massively multiplexed single-cell biomarker assay. Pure Appl. Chem. 2008: 80: 2627-2641.
Vaezeslami et al., Site-directed mutagenesis studies of tn5 transposase residues involved in synaptic complex formation. J Bacteriol. Oct. 2007;189(20):7436-41.

\* cited by examiner

TRANSPOSASE-MEDIATED IMAGING OF THE ACCESSIBLE GENOME

CROSS-REFERENCING

This application is a § 371 national phase of International Application No. PCT/US2017/021677, filed on Mar. 9, 2017, which claims the benefit of U.S. Provisional Application Ser. No. 62/306,504, filed Mar. 10, 2016, which applications are incorporated by reference in their entireties.

GOVERNMENT SUPPORT

This invention was made with government support under contract HG007735 awarded by the National Institutes of Health. The government has certain rights in the invention.

BACKGROUND

Eukaryotic genomes are extensively compacted in chromatin, except for active regulatory elements whose access control gene activity. These accessible elements comprise approximately 1% of the genome in any given cell types and include enhancers, promoters, and other regulatory sequences critical in development and disease. Nuclear architecture and 3D genome organization are tightly linked to gene expression, replication and DNA repair. Despite recent advances, current epigenomic methods extract regulatory DNA outside of the native context of the nucleus and reconstruct regulation on an imaginary linear genome, divorced from the intricate spatio-temporal organization evident in movies of living cells.

Thus, there remains a need for better epigenomic methods for studying the accessible genome.

SUMMARY

This disclosure provides, among other things, methods for labeling and analyzing the accessible genome using a transposase. The methods of the invention can be used to capture spatial information and map the positions of regulatory DNA in an intact live cell or fixed cell. In some embodiments, DNA from accessible chromatin regions can be both imaged and sequenced from a single sample. In addition, cells with their chromatin labeled by the methods of the invention can be sorted based on the status of their regulatory DNA.

In some embodiments, a method for detecting accessible chromatin is provided. In these embodiments, the method may comprise obtaining a transposase complex comprising a transposase bound to at least one DNA adapter, either of which comprises a detectable label; contacting chromatin with the transposase complex under conditions suitable for binding of the transposase to accessible regions in the chromatin; and detecting the detectable label. If the DNA adaptor comprises the detectable label, then the method may comprise: obtaining a transposase complex comprising a transposase bound to at least one DNA adapter that comprises a recognition sequence for the transposase and a detectable label, contacting chromatin with the transposase complex under conditions suitable for transposition, thereby joining the at least one DNA adapter with the chromatin at accessible regions in the chromatin; and detecting the label of the inserted DNA adapter. If the comprises the detectable label, then the method may comprise: obtaining a transposase complex comprising a transposase comprising a detectable label, wherein the transposase is bound to at least one DNA adapter that comprises a recognition sequence for the transposase; contacting chromatin with the transposase complex under conditions suitable for binding of the transposase to accessible regions in the chromatin; and detecting the label of the transposase.

The method may be performed on chromatin in situ inside a living cell or a fixed cell. Alternatively, the method may be performed on chromatin isolated from a cell.

In some embodiments, the transposase is a hyperactive transposase (i.e., comprising one or more mutations or chemical modifications that enhance its catalytic activity). In some embodiments, the transposase is a hyperactive Tn5 transposase.

In some embodiments, the DNA adapter comprises: i) a first oligonucleotide comprising the nucleotide sequence of SEQ ID NO:1 or a nucleotide sequence having at least 95% identity to the sequence of SEQ ID NO:1, and ii) a second oligonucleotide comprising a sequence sufficiently complementary to and capable of hybridizing with a portion of the first oligonucleotide such that the DNA adapter comprises at least a portion that is double-stranded, wherein the double stranded portion comprises the recognition sequence for the transposase. In some embodiments, the second oligonucleotide comprises a nucleotide sequence selected from the group consisting of SEQ ID NO:2 and SEQ ID NO:3, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the DNA adapter is capable of transposase catalyzed insertion into the accessible chromatin.

In some embodiments, the transposase complex comprises a transposase dimer bound to i) a first DNA adapter, wherein the first DNA adapter comprises a first recognition sequence for the transposase and a first detectable label, and ii) a second DNA adapter, wherein the second DNA adapter comprises a second recognition sequence for the transposase and a second detectable label. In one embodiment, the first DNA adapter comprises a first oligonucleotide comprising the nucleotide sequence of SEQ ID NO:1 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, and a second oligonucleotide comprising the nucleotide sequence of SEQ ID NO:2 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto. In another embodiment, the second DNA adapter comprises a first oligonucleotide comprising the nucleotide sequence of SEQ ID NO:1 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, and a second oligonucleotide comprising the nucleotide sequence of SEQ ID NO:3 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the first DNA adapter and the second DNA adapter are capable of transposase catalyzed insertion into the accessible chromatin.

In some embodiments, the first DNA adapter comprises a first oligonucleotide comprising the nucleotide sequence of SEQ ID NO:1 and a second oligonucleotide comprising the nucleotide sequence of SEQ ID NO:2, and the second DNA adapter comprises a first oligonucleotide comprising the nucleotide sequence of SEQ ID NO:1 and a second oligonucleotide comprising the nucleotide sequence of SEQ ID NO:3.

In some embodiments, the detectable label is a fluorophore, a metal particle, a magnetic particle, a mass tag, a chemiluminescent label, a ligand, a quantum dot, or a hapten. Detection of the labeled DNA adapter after its insertion into chromatin depends on the choice of label and can be performed in any number of ways. For example, if the DNA adapter is detectably labeled with a fluorophore, insertion of the DNA adapter at accessible sites in chromatin can be detected by performing fluorescence imaging. Alternatively, the DNA adapter may be detectably labeled with a metal particle, in which case, insertion of the DNA adapter at accessible sites in chromatin can be detected by performing electron microscopy or mass cytometry. In a further example, the DNA adapter may be detectably labeled with a ligand, in which case, insertion of the DNA adapter at accessible sites in chromatin can be detected using its binding partner (e.g., biotin-streptavidin, hapten-antibody, or enzyme-substrate). In yet another example, the DNA adapter may be detectably labeled with an enzyme, in which case, insertion of the DNA adapter at accessible sites in chromatin can be detected using a colorimetric or chemiluminescent assay (e.g., colorimetric assay with beta-galactosidase, chemiluminescent assay with horseradish peroxidase or alkaline phosphatase).

In some embodiments, the method further comprises identifying regulatory DNA (e.g., site of a promoter, enhancer, or insulator), a transcription factor binding site, or a nucleosome binding site in the accessible chromatin.

In some embodiments, the method further comprises mapping the positions of the sites that the DNA adapter inserts into the accessible chromatin.

In some embodiments, the method further comprises sequencing DNA at the sites where the DNA adapter inserts into the accessible chromatin.

In some embodiments, the method further comprises sorting cells based on labeling of their accessible chromatin by a method described herein.

A composition comprising a transposase complex is also provided. In these embodiments, the transposase complex may comprise a transposase bound to a DNA adapter, wherein either the transposase or DNA adaptor comprises a detectable label In some embodiments, the DNA adapter may comprise i) a first oligonucleotide comprising the nucleotide sequence of SEQ ID NO:1 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, and ii) a second oligonucleotide comprising a sequence sufficiently complementary to and capable of hybridizing with a portion of the first oligonucleotide such that the DNA adapter comprises at least a portion that is double-stranded, wherein the double stranded portion comprises a recognition sequence for the transposase, wherein the DNA adapter is capable of transposase catalyzed insertion into accessible chromatin.

In some embodiments, the DNA adapter comprises a detectable label selected from the group consisting of a fluorophore, a metal particle, a magnetic particle, an isotopic label, a quantum dot, a chemiluminescent label, a ligand, and a hapten.

In some embodiments, the transposase comprises a detectable label selected from the group consisting of a fluorophore, a metal particle, a magnetic particle, an isotopic label, a chemiluminescent label, a quantum dot, a ligand, and a hapten. In these embodiments, the detectable label may be directly lined to the transposase by reacting the transposase with an activated label (e.g., a maleimide-, iodoacetate-, succinimidyl-ester or isothiocyanate-label conjugate) or by adding an aldehyde tag to the transposase and then reacting the aldehyde tag with the fluorophore (see, e.g., Carrico et al. Nat Chem Biol 2007 3, 321-322 and Hudak Angew. Chem. Int. Ed. 2012 51, 4161-4165), for example. Alternatively, the transposase may be fused to a fluorescent protein or luciferase.

In some embodiments the transposase complex comprises a transposase dimer bound to two DNA adapters, wherein the first DNA adapter comprises a first recognition sequence for the transposase and a first detectable label, and the second DNA adapter comprises a second recognition sequence for the transposase and a second detectable label. In one embodiment, the first DNA adapter comprises a first oligonucleotide comprising the nucleotide sequence of SEQ ID NO:1 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, and a second oligonucleotide comprising the nucleotide sequence of SEQ ID NO:2 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto; and the second DNA adapter comprises the first oligonucleotide comprising the nucleotide sequence of SEQ ID NO:1 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, and a third oligonucleotide comprising the nucleotide sequence of SEQ ID NO:3 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto; wherein the first DNA adapter and the second DNA adapter are capable of transposase catalyzed insertion into the accessible chromatin.

In some embodiments, the first DNA adapter comprises a first oligonucleotide comprising the nucleotide sequence of SEQ ID NO:1 and a second oligonucleotide comprising the nucleotide sequence of SEQ ID NO:2, and the second DNA adapter comprises a first oligonucleotide comprising the nucleotide sequence of SEQ ID NO:1 and a second oligonucleotide comprising the nucleotide sequence of SEQ ID NO:3.

In another aspect, a kit comprising a transposase and at least one DNA adapter that comprises a recognition sequence for the transposase is provided. In these embodiments, either the DNA adaptor or the recognition sequence comprises a detectable label. The kit may further comprise written instructions for detecting accessible chromatin.

These and other embodiments of the subject invention will readily occur to those of skill in the art in view of the disclosure herein.

BRIEF DESCRIPTION OF THE FIGURES

The skilled artisan will understand that the drawings, described below, are for illustration purposes only. The drawings are not intended to limit the scope of the present teachings in any way

DETAILED DESCRIPTION

Figure 1:
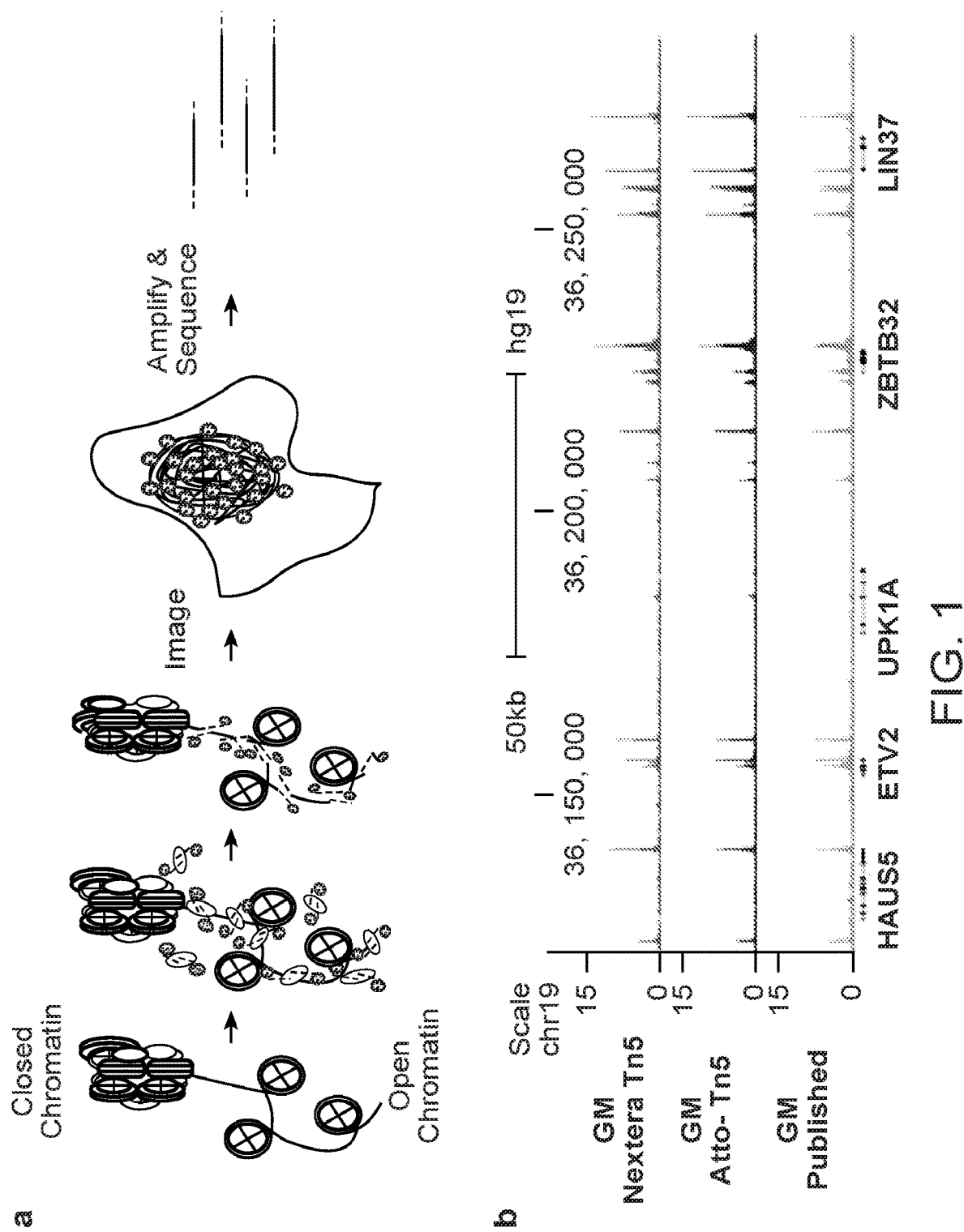
FIG. 1: ATAC-see visualizes the accessible genome in situ. Panel a, Schematic of ATAC-see. Panel b, Genome browser tracks of ATAC-seq libraries from GM12878 cells (GM) generated by using different Tn5 transposases: green: Nextera Tn5, blue: Atto-Tn5, orange: previously published data. Panel c, Left panel: Genome-wide comparison of ATAC-seq reads of GM12878 libraries (GM)prepared by either using Nextera Tn5 or Atto-Tn5. Right panel: TSS enrichment of GM12878 ATAC-seq libraries transposed with different Tn5. Green=Nextera Tn5, blue (Atto)=Atto-Tn5, orange=previously published data. Panel d, Genome-wide comparison of ATAC-seq reads of HT1080 library prepared in no fixation and with fixation. Left: Scatter plot of all data points. Right: Metagene analysis centered on transcriptional start sites (TSS).
Figure 1:
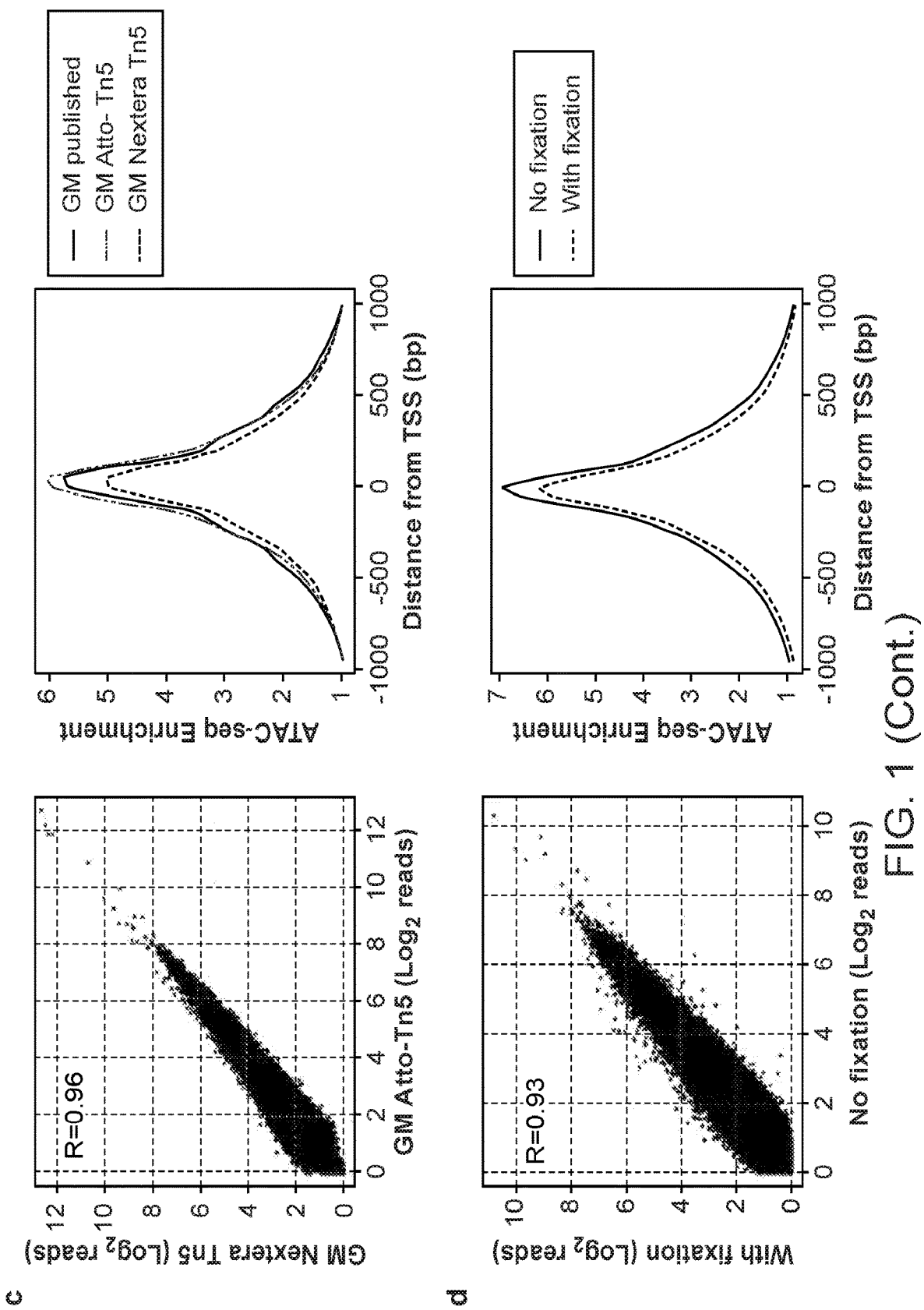

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that, as used in this specification and the appended claims, the singular forms "a," "an" and "the" include plural referents unless the content clearly dictates otherwise. Thus, for example, reference to "a transposase" includes two or more transposases, and the like.

A method for detecting accessible chromatin is provided. As noted above, in some embodiments, the method may comprise obtaining a transposase complex that comprises a transposase bound to at least one DNA adapter (which may be 40 to 150 bases in length, e.g., 50 to 120 bases, although adaptors outside of this range are envisioned) that comprises a recognition sequence for the transposase, where either the transposase or DNA adaptor comprises a detectable label. As would be recognized, the transposon recognition sequence (also known as a transposon end sequence) is a double-stranded sequence to which a transposase (e.g., a Tn5 transposase or variant thereof) binds. The Tn5 transposon recognition sequence is 19 bp in length (see, e.g., Vaez-eslami et al, J. Bacteriol. 2007 189 20: 7436-7441), although many others are known and may be 18-20 bp, e.g., 19 bp in length. In these embodiments, the transposase complex comprises a transposase loaded with either a single adaptor molecule that contains a recognition sequence for the transposase at both ends, or two adaptor molecule that each contain a recognition sequence for the transposase at one end. The latter type can be used of the chromatin is going to be sequenced by ATAC-seq (Buenrostro et al, Nature Methods 2013 10: 1213-1218). Such complexes can be combined with chromatin to add the adaptor molecule to the chromatin at accessible sites. If a transposase complex contains a single adaptor molecule that contains a transposon recognition sequence at both ends, the adaptor molecule will be inserted into the chromatin. If a transposase complex contains a two adaptor molecules that contains a transposon recognition sequence at one end, the transposase catalyzes simultaneous fragmentation of the chromatin and tagging of the fragments with sequences that are adjacent to the transposon recognition sequence (i.e., by "tagmentation"). Systems for tagmentation are described in a variety of publications, including Caruccio (Methods Mol. Biol. 2011 733: 241-55) and US20100120098, which are incorporated by reference herein. In some cases, the transposase enzyme can insert the nucleic acid sequence into the polynucleotide in a substantially sequence-independent manner. The transposase can be prokaryotic, eukaryotic or from a virus. Methods for tagmenting, as well as transposon end sequences, are well known in the art (see, e.g., Picelli et al, Genome Res. 2014 24: 2033-40; Adey et al, Genome Biol. 2010 11:R119 and Caruccio et al, Methods Mol. Biol. 2011 733: 241-55, US20100120098 and US20130203605). Kits for performing tagmentation are commercially sold under the tradename NEXTERA™ by Illumina (San Diego, Calif.). This initial step of the method may be done by loading a transposase with oligonucleotides that have been annealed together so that at least the transposase recognition sequence is double stranded.

The adaptors used in the method are typically made of oligonucleotides that have been annealed together, where an oligonucleotide is a single-stranded multimer of nucleotide that is from about 2 to 200 nucleotides in length, up to 500 nucleotides in length. Oligonucleotides may be synthetic or may be made enzymatically and, in some embodiments, are 30 to 150 nucleotides in length. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

In some embodiments, the DNA adapter may comprise i) a nucleotide sequence having at least 95% identity to the sequence of SEQ ID NO:1, and ii) a second oligonucleotide comprising a sequence sufficiently complementary to and capable of hybridizing with a portion of the first oligonucleotide such that the DNA adapter comprises at least a portion that is double-stranded, wherein the double stranded portion comprises the recognition sequence for the transposase. In these embodiments, the second oligonucleotide may comprise a nucleotide sequence having at least 95% identity to a sequence selected from the group consisting of SEQ ID NO:2 and SEQ ID NO:3, wherein the DNA adapter is capable of transposase catalyzed insertion into the accessible chromatin.

In some embodiments, the transposase complex may comprise a transposase dimer bound to i) a first DNA adapter, wherein the first DNA adapter comprises a first recognition sequence for the transposase and a first detectable label, and ii) a second DNA adapter, wherein the second DNA adapter comprises a second recognition sequence for the transposase and a second detectable label. In these embodiments, the first DNA adapter may comprises a first oligonucleotide comprising a nucleotide sequence having at least 95% identity to the sequence of SEQ ID NO:1 and a second oligonucleotide comprising a nucleotide sequence having at least 95% identity to the sequence of SEQ ID NO:2; and the second DNA adapter comprises the first oligonucleotide comprising a nucleotide sequence having at least 95% identity to the sequence of SEQ ID NO:1 and a third oligonucleotide comprising a nucleotide sequence having at least 95% identity to the sequence of SEQ ID NO:3; wherein the first DNA adapter and the second DNA adapter are capable of transposase catalyzed insertion into the accessible chromatin. In these embodiments, the first DNA adapter may comprise a first oligonucleotide comprising the nucleotide sequence of SEQ ID NO:1 and a second oligonucleotide comprising the nucleotide sequence of SEQ ID NO:2, and the second DNA adapter comprises a first oligonucleotide comprising the nucleotide sequence of SEQ ID NO:1 and a second oligonucleotide comprising the nucleotide sequence of SEQ ID NO:3.

In some embodiments, the adaptor is linked to a detectable label, e.g., at a 3' end, at a 5' end, or anywhere in between. In some embodiments, the detectable label may be linked to a nucleotide in the transposase recognition sequence. In other embodiments, the detectable label may be linked to a nucleotide that is not in the transposase recognition sequence.

In some embodiments, the transposase may comprise a detectable label. In these embodiments, the transposase may be labeled with a detectable label or may be a fusion protein, where the fusion partner may be a fluorescent protein or luciferase.

A detectable label is a moiety that is readily detected by optical means, e.g., light-generating or fluorescent labels. Detectable labels may be directly detectable and, as such, may be fluorescent or luminescent (e.g., chemiluminescent, etc.) or indirectly detectable and, as such, may contain a detectable moiety such as e.g., biotin. Fluorphores are capable of exhibiting fluorescence in the detectable range. Particular examples of labels which may be used in the practice of the invention include, but are not limited to, an ATTO dye such as ATTO 390, ATTO 425, ATTO 488, ATTO 520, ATTO 590, ATTO 655, and ATTO 680, a SYBR dye such as SYBR green and SYBR gold, a CAL Fluor dye such as CAL Fluor Gold 540, CAL Fluor Orange 560, CAL Fluor Red 590, CAL Fluor Red 610, and CAL Fluor Red 635, a QUASAR dye such as QUASAR 570, QUASAR 670, and QUASAR 705, an ALEXA Fluor such as ALEXA Fluor 350, ALEXA Fluor 488, ALEXA Fluor 546, ALEXA Fluor 555, ALEXA Fluor 594, ALEXA Fluor 647, and ALEXA Fluor 784, a cyanine dye such as Cy 3, Cy3.5, Cy5, Cy5.5, and Cy7, fluorescein, 2', 4', 5', 7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), rhodamine, carboxy-X-rhodamine (ROX), tetramethyl rhodamine (TAMRA), FITC, dansyl, umbelliferone, dimethyl acridinium ester (DMAE), Texas red, luminol, NADPH, horseradish peroxidase (HRP), α-β-galactosidase, ferritin, and metal particles such as platinum, platinum-palladium, gold-palladium, tungsten-tantalum, tungsten, colloidal gold, silver, titanium, lead, and uranium particles.

As used herein, the term "mass tagged" refers to a molecule that is tagged with either a single kind of stable isotope that is identifiable by its unique mass or mass profile or a combination of the same. An element may exist as one or more isotopes, and this term also includes isotopes of positively and negatively metals. The terms "mass tagged" and "elementally tagged" may be used interchangeably herein. A mass tag may include transition metals, post transition metals, halides, noble metal or lanthanide, that is identifiable by its mass, distinguishable from other mass tags, and used to tag a biologically active material or analyte. A mass tag has an atomic mass that is distinguishable from the atomic masses present in the analytical sample and in the particle of interest. The term "monoisotopic" means that a tag contains a single type of metal isotope (although any one tag may contain multiple metal atoms of the same type). Methods for adding mass tags to other molcules are described in US20150080233, for example.

The general principles of mass cytometry, including methods by which single cell suspensions can be made, methods by which cells can be labeled using, e.g., mass-tagged antibodies, methods for atomizing particles and methods for performing elemental analysis on particles, as well as hardware that can be employed in mass cytometry, including flow cells, ionization chambers, reagents, mass spectrometers and computer control systems are known and are reviewed in a variety of publications including, but not limited to Bandura et al Analytical Chemistry 2009 81 6813-6822), Tanner et al (Pure Appl. Chem 2008 80: 2627-2641), U.S. Pat. No. 7,479,630 (Method and apparatus for flow cytometry linked with elemental analysis) and U.S. Pat. No. 7,135,296 (Elemental analysis of tagged biologically active materials); and published U.S. patent application 20080046194, for example, which publications are incorporated by reference herein for disclosure of those methods and hardware.

Examples of transposases include, but are not limited to, Tn transposase (e.g. Tn3, Tn5, Tn7, Tn10, Tn552, Tn903), a MuA transposase, a Vibhar transposase (e.g. from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Te1, THE-1, Tn/O, TnA, Tn3, Tn5, Tn7, Tn10, Tn552, Tn903, Tol1, Tol2, TnlO, Ty1, any prokaryotic transposase, or any transposase related to and/or derived from those listed above. In certain instances, a transposase related to and/or derived from a parent transposase can comprise a peptide fragment with at least about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% amino acid sequence homology to a corresponding peptide fragment of the parent transposase. The peptide fragment can be at least about 10, about 15, about 20, about 25, about 30, about 35, about 40, about 45, about 50, about 60, about 70, about 80, about 90, about 100, about 150, about 200, about 250, about 300, about 400, or about 500 amino acids in length. For example, a transposase derived from Tn5 can comprise a peptide fragment that is 50 amino acids in length and about 80% homologous to a corresponding fragment in a parent Tn5 transposase. In some cases, the insertion can be facilitated and/or triggered by addition of one or more cations. The cations can be divalent cations such as, for example, $Ca^{2+}$, $Mg^{2+}$ and $Mn^{2+}$.

After the transposase is loaded with adaptor, the transposes complex is contacted with chromatin under conditions suitable for binding of the transposase to the chromatin (i.e., a suitable temperature, time and conditions that result in a reaction, e.g., binding and/or cleavage/ligation). In some cases, the contacting may be done under conditions suitable for transposition, the thereby joining the at least one DNA adapter with the chromatin at sites that are accessible to the transposase. In these embodiments, the term "chromatin accessibility" refers to how accessible a nucleic acid site is within a polynucleotide, such as in genomic DNA, i.e., how "open" the chromatin is. A nucleic acid site associated with a polypeptide, such as with genomic DNA in nucleosomes, is usually inaccessible. A nucleic acid site not complexed with a polypeptide is generally accessible, such as with genomic DNA between nucleosomes (with the exception of nucleic acid sites complexed with transcription factors and other DNA binding proteins). In some cases, a cell sample can be optionally fixed and/or permeabilized to allow access to its chromatin. The permeabilization can be performed in a way to minimally perturb the nuclei in the cell. In some instances, the cell sample can be permeabilized using a permeabilization agent, examples of which include, but are not limited to, NP40, digitonin, tween, streptolysin, and cationic lipids. In other instances, the calls can be permeabilized using hypotonic shock and/or ultrasonication. In other cases, the transposase can be highly charged, which may allow it to pass through cell membranes.

After the transposase reaction the method may comprise detecting the label of the inserted DNA adapter or the transposase. This may be done using any suitable method, including by flow cytometry, fluorescent microscopy, electron microscopy or mass cytometry. If labels are detected by flow cytometry, the data may be shown as a scatter plot. If labels are detected by fluorescence imaging, the data may be shown as an image of at least the nucleus of a cell. Analysis of such data may reveal a pattern of labeling, e.g., a pattern within a cell or a population of cells.

The method may be performed on a population of cells. In some embodiments, the cells may be on a planar surface, e.g., of a microscope slide. In these embodiments, the cells may have been grown as a monolayer on the surface, grown in a liquid culture and then placed on the surface, or may in a tissue section that has been placed on the surface.

The population of cells used in the may may be composed of any number of cells, e.g., about 500 to about $10^6$ or more cells, about 500 to about 100,000 cells, about 500 to about 50,000 cells, about 500 to about 10,000 cells, about 50 to 1000 cells, about 1 to 500 cells, about 1 to 100 cells, about 1 to 50 cells, or a single cell. In some cases, the cell sample can consist of less than about 1000, about 2000, about 3000, about 4000, about 5000, about 6000, about 7000, about 8000, about 9000, about 10,000, about 15,000, about 20,000, about 25,000, about 30,000, about 40,000, about 50,000, about 60,000, about 70,000, about 80,000, about 90,000, about 100,000, about 120,000, about 140,000, about 160,000, about 180,000, about 200,000, about 250,000, about 300,000, about 350,000, about 400,000, about 450,000, about 500,000, about 600,000, about 700,000, about 800,000, about 900,000, or about 1,000,000 cells. In other cases, the cell sample can consist of more than about 1000, about 2000, about 3000, about 4000, about 5000, about 6000, about 7000, about 8000, about 9000, about 10,000, about 15,000, about 20,000, about 25,000, about 30,000, about 40,000, about 50,000, about 60,000, about 70,000, about 80,000, about 90,000, about 100,000, about 120,000, about 140,000, about 160,000, about 180,000, about 200,000, about 250,000, about 300,000, about 350,000, about 400,000, about 450,000, about 500,000, about 600,000, about 700,000, about 800,000, about 900,000, or about 1,000,000 cells.

The cells can be from any source. In certain cases, the cells may be obtained from a culture of cells, e.g., a cell line. In other cases, the cells may be isolated from an individual (e.g., a patient or the like). The cells may be isolated from a soft tissue or from a bodily fluid, or from a cell culture that is grown in vitro. In particular embodiments, the chromatin may be isolated from a soft tissue such as brain, adrenal gland, skin, lung, spleen, kidney, liver, spleen, lymph node, bone marrow, bladder stomach, small intestine, large intestine or muscle, etc. Bodily fluids include blood, plasma, saliva, mucous, phlegm, cerebral spinal fluid, pleural fluid, tears, lactal duct fluid, lymph, sputum, cerebrospinal fluid, synovial fluid, urine, amniotic fluid, and semen, etc.

In some embodiments, the chromatin analyzed in the method may be from blood cells, wherein blood cells refers to a sample of whole blood or a sub-population of cells in whole blood. Sub-populations of cells in whole blood include platelets, red blood cells (erythrocytes), platelets and white blood cells (i.e., peripheral blood leukocytes, which are made up of neutrophils, lymphocytes, eosinophils, basophils and monocytes). These five types of white blood cells can be further divided into two groups, granulocytes (which are also known as polymorphonuclear leukocytes and include neutrophils, eosinophils and basophils) and mononuclear leukocytes (which include monocytes and lymphocytes). Lymphocytes can be further divided into T cells, B cells and NK cells. Peripheral blood cells are found in the circulating pool of blood and not sequestered within the lymphatic system, spleen, liver, or bone marrow. Other cells are present in blood that can be isolated. If blood is first contacted with an agent and then a sample of the blood is used in an assay, then a portion or all of the contacted blood may be used in the method.

In certain embodiments, the cells can be isolated directly from a primary source. For example, the cell sample can be isolated directly from fresh tissues. In other cases, the cell sample can be isolated directly from frozen tissues. In yet other cases, the cell sample can be isolated directly from fixed tissues. Further examples of primary sources of cell samples include, but are not limited to, cells dissociated from tissues, blood cells, cells in an FFPE section, etc. In some embodiments, the transposase complex may be directly contacted with a tissue sample, In some embodiments, the cells analyzed are of the same cell type. In these embodiments, the population of cells may be cultured cells or selected by MACS or FACS from a heterogeneous population of cells, e.g., blood, by known methods using labeled antibodies to cells surface markers. A wide variety of cells can be isolated using these methods, including stem cells, cancer stem cells and subsets of blood cells. In particular embodiments the following cells may be isolated from blood by FACS or MACS; T cells ($CD3^+$ $CD4^+$ $CD8^+$), B cells ($CD19^+$ $CD20^+$), dendritic cells ($CD11c^+$ $CD20^+$), NK Cell ($CD56^+$), stem cells/precursor cells ($CD34^+$; hematopoietic stem cells only), macrophage/monocytes ($CD14^+$ $CD33^+$), granulocytes ($CD66b^+$), platelet ($CD41^+$ $CD61^+$ $CD62^+$), erythrocytes ($CD235a^+$), endothelial cells ($CD146^+$) and epithelial cells ($CD326^+$). Subsets of these cells can be isolated using antibodies to further cell surface markers.

In some embodiments, the method can be used to compare two samples. In these embodiments, the method may comprise analyzing a first population of cells using the above-described method to produce a first data set; and analyzing a second population of cells using the above-described method to produce a second data set; and comparing the first data set to the second data set, e.g., to see if there are any changes in in the localization of accessible chromatin, for example.

In some embodiments, the first population of cells and the second population of cells are collected from the same individual at different times. In other embodiments, the first population of cells and the second population of cells are different populations of cells collected from tissues or different individuals.

Exemplary cell types that can be used in the method include, for example, cells isolated from a tissue biopsy (e.g., from a tissue having a disease such as colon, breast, prostate, lung, skin cancer, or infected with a pathogen etc.) and normal cells from the same tissue, e.g., from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and normal cells (e.g., cells that are otherwise identical to the experimental cells except that they are not immortalized, infected, or treated, etc.); cells isolated from a mammal with a cancer, a disease, a geriatric mammal, or a mammal exposed to a condition, and cells from a mammal of the same species, e.g., from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be compared. In another embodiment, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells. Cells from yeast, plants and animals, such as fish, birds, reptiles, amphibians and mammals may be used in the subject methods. In certain embodiments, mammalian cells, i.e., cells from mice, rabbits, primates, or humans, or cultured derivatives thereof, may be used.

In some exemplary embodiments, the method may be used to identify the effect of a test agent, e.g., a drug, or to determine if there are differences in the effect of two or more different test agents. In these embodiments, two or more identical populations of cells may be prepared and, depending on how the experiment is to be performed, one or more of the populations of cells may be incubated with the test agent for a defined period of time. After incubation with the test agent, the chromatin of the populations of cells can be analyzed using the methods set forth above, and the results can be compared. In a particular embodiment, the cells may be blood cells, and the cells can be incubated with the test agent ex vivo. These methods can be used to determine the mode of action of a test agent, to identify changes in chromatin accessability in response to the drug, for example.

The method described above may also be used as a diagnostic (which term is intended to include methods that provide a diagnosis as well as methods that provide a prognosis). These methods may comprise, e.g., analyzing chromatin from a patient using the method described above to produce data; and providing a diagnosis or prognosis based on the data.

The method set forth herein may be used to provide a reliable diagnostic to any condition associated with, e.g., altered chromatin accessability. The method can be applied to the characterization, classification, differentiation, grading, staging, diagnosis, or prognosis of a condition characterized by an epigenetic pattern (e.g., a pattern of chromatin accessibility). For example, the method can be used to determine whether the pattern of labeling of a sample from an individual suspected of being affected by a disease or condition is the same or different compared to a pattern of labeling for a sample that is considered "normal" with respect to the disease or condition. In particular embodiments, the method can be directed to diagnosing an individual with a condition that is characterized by particular pattern of labeling, where the pattern is correlated with the condition. The methods can also be used for predicting the susceptibility of an individual to a condition.

Exemplary conditions that are suitable for analysis using the methods set forth herein can be, for example, cell proliferative disorder or predisposition to cell proliferative disorder; metabolic malfunction or disorder; immune malfunction, damage or disorder; CNS malfunction, damage or disease; symptoms of aggression or behavioral disturbance; clinical, psychological and social consequences of brain damage; psychotic disturbance and personality disorder; dementia or associated syndrome; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, the muscles, the connective tissue or the bones; endocrine and metabolic malfunction, damage or disease; headache or sexual malfunction, and combinations thereof.

In some embodiments, the method can provide a prognosis, e.g., to determine if a patient is at risk for recurrence. Cancer recurrence is a concern relating to a variety of types of cancer. The prognostic method can be used to identify surgically treated patients likely to experience cancer recurrence so that they can be offered additional therapeutic options, including preoperative or postoperative adjuncts such as chemotherapy, radiation, biological modifiers and other suitable therapies. The methods are especially effective for determining the risk of metastasis in patients who demonstrate no measurable metastasis at the time of examination or surgery.

The method can also be used as a theranostic, i.e., to provide a recommendation for a course of treatment for a patient having a disease or condition, e.g., a patient that has cancer. A course of treatment refers to the therapeutic measures taken for a patient after diagnosis or after treatment. For example, a determination of the likelihood for recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated.

In a particular embodiment, a lab will receive a sample (e.g., blood) from a remote location (e.g., a physician's office or hospital), the lab will analyze cells in the sample as described above to produce data, and the data may be forwarded to the remote location for analysis.

An adaptor comprising a double-stranded transposase recognition sequence and a detectable label are also provided. One of the strands of the transposase recognition sequence may have the sequence of SEQ ID NO: 1. The adaptor may be linked to the detectable label, e.g., at a 3' end, at a 5' end, or anywhere in between. In some embodiments, the detectable label may be linked to a nucleotide in the transposase recognition sequence. In other embodiments, the detectable label may be linked to a nucleotide that is not in the transposase recognition sequence.

Also provided is a composition comprising a transposase complex comprising a transposase bound to a DNA adapter, wherein either the transposase or DNA adaptor comprises a detectable label. In some embodiments, the transposase complex may comprise a transposase that comprises a detectable label In some embodiments, the transposase complex may comprise a transposase bound to a DNA adapter comprising a detectable label. In these embodiments, the DNA adapter may comprises i) a first oligonucleotide comprising the nucleotide sequence of SEQ ID NO:1 or a nucleotide sequence having at least 95% identity to the sequence of SEQ ID NO:1, and ii) a second oligonucleotide comprising a sequence sufficiently complementary to and capable of hybridizing with a portion of the first oligonucleotide such that the DNA adapter comprises at least a portion that is double-stranded, wherein the double stranded portion comprises a recognition sequence for the transposase, wherein the DNA adapter is capable of transposase catalyzed insertion into accessible chromatin. In these embodiments, the transposase complex comprises a transposase dimer bound to two DNA adapters, wherein the first DNA adapter comprises a first recognition sequence for the transposase and a first detectable label, and the second DNA adapter comprises a second recognition sequence for the transposase and a second detectable label. THe first DNA adapter may comprise a first oligonucleotide comprising the nucleotide sequence of SEQ ID NO:1 or a nucleotide sequence having at least 95% identity to the sequence of SEQ ID NO:1 and a second oligonucleotide comprising the nucleotide sequence of SEQ ID NO:2 or a nucleotide sequence having at least 95% identity to the sequence of SEQ ID NO:2; and the second DNA adapter comprises the first oligonucleotide comprising the nucleotide sequence of SEQ ID NO:1 or a nucleotide sequence having at least 95% identity to the sequence of SEQ ID NO:1 and a third oligonucleotide comprising the nucleotide sequence of SEQ ID NO:3 or a nucleotide sequence having at least 95% identity to the sequence of SEQ ID NO:3; wherein the first DNA adapter and the second DNA adapter are capable of transposase catalyzed insertion into the accessible chromatin. In these embodiments, the first DNA adapter comprises a first oligonucleotide comprising the nucleotide sequence of SEQ ID NO:1 and a second oligonucleotide comprising the nucleotide sequence of SEQ ID NO:2, and the second DNA adapter comprises a first oligonucleotide comprising the nucleotide sequence of SEQ ID NO:1 and a second oligonucleotide comprising the nucleotide sequence of SEQ ID NO:3. The detectable label is a fluorophore, a metal particle, a magnetic particle, an isotopic label, a chemiluminescent label, a ligand, or a hapten.

Also provided by this disclosure are kits that comprise a transposase and at least one DNA adapter that comprises a recognition sequence for the transposase, wherein either the DNA adaptor or the recognition sequence comprises a detectable label. In some embodiments, the kit may comprise instruction for detecting accessible chromatin. In some embodiments, the kit may comprise a hyperactive transposase and at least one DNA adapter, said DNA adapter comprising a recognition sequence for the transposase and a detectable label. The at least one DNA adapter may comprise a first DNA adapter comprising a first oligonucleotide comprising the nucleotide sequence of SEQ ID NO:1 or a nucleotide sequence having at least 95% identity to the sequence of SEQ ID NO:1 and a second oligonucleotide comprising the nucleotide sequence of SEQ ID NO:2 or a nucleotide sequence having at least 95% identity to the sequence of SEQ ID NO:2, and a second DNA adapter comprising a first oligonucleotide comprising the nucleotide sequence of SEQ ID NO:1 or a nucleotide sequence having at least 95% identity to the sequence of SEQ ID NO:1 and a second oligonucleotide comprising the nucleotide sequence of SEQ ID NO:3 or a nucleotide sequence having at least 95% identity to the sequence of SEQ ID NO:3. The at least one DNA adapter may comprise a first DNA adapter comprising a first oligonucleotide comprising the nucleotide sequence of SEQ ID NO:1 and a second oligonucleotide comprising the nucleotide sequence of SEQ ID NO:2, and a second DNA adapter comprising a first oligonucleotide comprising the nucleotide sequence of SEQ ID NO:1 and a second oligonucleotide comprising the nucleotide sequence of SEQ ID NO:3.

The various components of the kit may be present in separate containers or certain compatible components may be precombined into a single container, as desired. In addition to the probe, the kit may contain any of the additional components used in the method described above, e.g., a buffer, etc.

In addition to above-mentioned components, the subject kits may further include instructions for using the components of the kit to practice the subject methods, i.e., instructions for sample analysis.

EMBODIMENTS

Embodiment 1

A method for detecting accessible chromatin, the method comprising: a) providing a transposase complex comprising a transposase bound to at least one DNA adapter, wherein the DNA adapter comprises a recognition sequence for the transposase and a detectable label; b) contacting chromatin with the transposase complex, whereby said at least one DNA adapter is inserted into the chromatin at sites that are accessible to the transposase; and c) detecting the label of the inserted DNA adapter.

Embodiment 2

The method of embodiment 1, wherein the transposase is a hyperactive Tn5 transposase.

Embodiment 3

The method of embodiment 2, wherein the DNA adapter comprises i) a first oligonucleotide comprising the nucleotide sequence of SEQ ID NO:1 or a nucleotide sequence having at least 95% identity to the sequence of SEQ ID NO:1, and ii) a second oligonucleotide comprising a sequence sufficiently complementary to and capable of hybridizing with a portion of the first oligonucleotide such that the DNA adapter comprises at least a portion that is double-stranded, wherein the double stranded portion comprises the recognition sequence for the transposase.

Embodiment 4

The method of embodiment 3, wherein the second oligonucleotide comprises a nucleotide sequence selected from the group consisting of SEQ ID NO:2 and SEQ ID NO:3, or a nucleotide sequence having at least 95% identity to a sequence selected from the group consisting of SEQ ID NO:2 and SEQ ID NO:3, wherein the DNA adapter is capable of transposase catalyzed insertion into the accessible chromatin.

Embodiment 5

The method of embodiment 1, wherein the transposase complex comprises a transposase dimer bound to i) a first DNA adapter, wherein the first DNA adapter comprises a first recognition sequence for the transposase and a first detectable label, and ii) a second DNA adapter, wherein the second DNA adapter comprises a second recognition sequence for the transposase and a second detectable label.

Embodiment 6

The method of embodiment 5, wherein the first DNA adapter comprises a first oligonucleotide comprising the nucleotide sequence of SEQ ID NO:1 or a nucleotide sequence having at least 95% identity to the sequence of SEQ ID NO:1 and a second oligonucleotide comprising the nucleotide sequence of SEQ ID NO:2 or a nucleotide sequence having at least 95% identity to the sequence of SEQ ID NO:2; and the second DNA adapter comprises the first oligonucleotide comprising the nucleotide sequence of SEQ ID NO:1 or a nucleotide sequence having at least 95% identity to the sequence of SEQ ID NO:1 and a third oligonucleotide comprising the nucleotide sequence of SEQ ID NO:3 or a nucleotide sequence having at least 95% identity to the sequence of SEQ ID NO:3; wherein the first DNA adapter and the second DNA adapter are capable of transposase catalyzed insertion into the accessible chromatin.

Embodiment 7

The method of embodiment 6, wherein the first DNA adapter comprises a first oligonucleotide comprising the nucleotide sequence of SEQ ID NO:1 and a second oligonucleotide comprising the nucleotide sequence of SEQ ID NO:2, and the second DNA adapter comprises a first oligonucleotide comprising the nucleotide sequence of SEQ ID NO:1 and a second oligonucleotide comprising the nucleotide sequence of SEQ ID NO:3.

Embodiment 8

The method of embodiment 1, wherein the detectable label is a fluorophore, a metal particle, a magnetic particle, an isotopic label, a chemiluminescent label, a ligand, or a hapten.

Embodiment 9

The method of embodiment 8, wherein the fluorophore is an ATTO fluorescent dye.

Embodiment 10

The method of embodiment 8, wherein said detecting comprises performing fluorescence imaging.

Embodiment 11

The method of embodiment 8, wherein said detecting comprises performing electron microscopy.

Embodiment 12

The method of embodiment 1, further comprising identifying regulatory DNA, a transcription factor binding site, or a nucleosome binding site in the accessible chromatin.

Embodiment 13

The method of embodiment 12, wherein the regulatory DNA comprises a promoter, enhancer, or insulator.

Embodiment 14

The method of embodiment 1, further comprising mapping the positions of the sites that the DNA adapter inserts into the accessible chromatin.

Embodiment 15

The method of embodiment 1, further comprising sequencing DNA at the sites where the DNA adapter inserts into the accessible chromatin.

Embodiment 16

The method of embodiment 1, wherein the method is performed on chromatin in situ inside a living cell or a fixed cell.

Embodiment 17

The method of embodiment 1, wherein the method is performed on isolated chromatin.

Embodiment 18

The method of embodiment 1, further comprising sorting cells based on labeling of their accessible chromatin by the DNA adapter.

Embodiment 19

A composition comprising a transposase complex comprising a transposase bound to a DNA adapter comprising a detectable label, wherein the DNA adapter comprises i) a first oligonucleotide comprising the nucleotide sequence of SEQ ID NO:1 or a nucleotide sequence having at least 95% identity to the sequence of SEQ ID NO:1, and ii) a second oligonucleotide comprising a sequence sufficiently complementary to and capable of hybridizing with a portion of the first oligonucleotide such that the DNA adapter comprises at least a portion that is double-stranded, wherein the double stranded portion comprises a recognition sequence for the transposase, wherein the DNA adapter is capable of transposase catalyzed insertion into accessible chromatin.

Embodiment 20

The composition of embodiment 19, wherein the transposase complex comprises a transposase dimer bound to two DNA adapters, wherein the first DNA adapter comprises a first recognition sequence for the transposase and a first detectable label, and the second DNA adapter comprises a second recognition sequence for the transposase and a second detectable label.

Embodiment 21

The composition of embodiment 20, wherein the first DNA adapter comprises a first oligonucleotide comprising the nucleotide sequence of SEQ ID NO:1 or a nucleotide sequence having at least 95% identity to the sequence of SEQ ID NO:1 and a second oligonucleotide comprising the nucleotide sequence of SEQ ID NO:2 or a nucleotide sequence having at least 95% identity to the sequence of SEQ ID NO:2; and the second DNA adapter comprises the first oligonucleotide comprising the nucleotide sequence of SEQ ID NO:1 or a nucleotide sequence having at least 95% identity to the sequence of SEQ ID NO:1 and a third oligonucleotide comprising the nucleotide sequence of SEQ ID NO:3 or a nucleotide sequence having at least 95% identity to the sequence of SEQ ID NO:3; wherein the first DNA adapter and the second DNA adapter are capable of transposase catalyzed insertion into the accessible chromatin.

Embodiment 22

The composition of embodiment 21, wherein the first DNA adapter comprises a first oligonucleotide comprising the nucleotide sequence of SEQ ID NO:1 and a second oligonucleotide comprising the nucleotide sequence of SEQ ID NO:2, and the second DNA adapter comprises a first oligonucleotide comprising the nucleotide sequence of SEQ ID NO:1 and a second oligonucleotide comprising the nucleotide sequence of SEQ ID NO:3.

Embodiment 23

The composition of embodiment 19, wherein the detectable label is a fluorophore, a metal particle, a magnetic particle, an isotopic label, a chemiluminescent label, a ligand, or a hapten.

Embodiment 24

A kit comprising the composition of embodiment 19 and instructions for detecting accessible chromatin.

Embodiment 25

A kit comprising a hyperactive transposase and at least one DNA adapter, said DNA adapter comprising a recognition sequence for the transposase and a detectable label.

Embodiment 26

The kit of embodiment 25, wherein said at least one DNA adapter comprises a first DNA adapter comprising a first oligonucleotide comprising the nucleotide sequence of SEQ ID NO:1 or a nucleotide sequence having at least 95% identity to the sequence of SEQ ID NO:1 and a second oligonucleotide comprising the nucleotide sequence of SEQ ID NO:2 or a nucleotide sequence having at least 95% identity to the sequence of SEQ ID NO:2, and a second DNA adapter comprising a first oligonucleotide comprising the nucleotide sequence of SEQ ID NO:1 or a nucleotide sequence having at least 95% identity to the sequence of SEQ ID NO:1 and a second oligonucleotide comprising the nucleotide sequence of SEQ ID NO:3 or a nucleotide sequence having at least 95% identity to the sequence of SEQ ID NO:3.

Embodiment 27

The kit of embodiment 26, wherein said at least one DNA adapter comprises a first DNA adapter comprising a first oligonucleotide comprising the nucleotide sequence of SEQ ID NO:1 and a second oligonucleotide comprising the nucleotide sequence of SEQ ID NO:2, and a second DNA adapter comprising a first oligonucleotide comprising the nucleotide sequence of SEQ ID NO:1 and a second oligonucleotide comprising the nucleotide sequence of SEQ ID NO:3.

Aspects of the present teachings can be further understood in light of the following examples, which should not be construed as limiting the scope of the present teachings in any way.

EXAMPLES

Spatial organization of the genome plays central roles in gene expression, DNA replication, and repair. But current epigenomic approaches largely map DNA regulatory elements without the native context of the nucleus. Described herein is a technique referred to as ATAC-see (Assay of Transposase-Accessible Chromatin with visualization), a transposase-mediated imaging technology that enables direct imaging of the accessible genome in situ, cell sorting, and deep sequencing to reveal the identity of the imaged elements. ATAC-see revealed the cell type-specific spatial organization of the accessible genome and the coordinated process of neutrophil extrusion of its chromatin (NETosis). Integration of ATAC-see with flow cytometry enables automated quantitation and prospective cell isolation as a function of chromatin accessibility, and reveals a cell cycle dependence of chromatin accessibility that is especially dynamic in G1 phase. The integration of imaging and epigenomics provides a general and scalable approach for deciphering the spatio-temporal architecture of gene control.

ATAC-see unveils the spatial organization of the accessible genome in its native context for any cell type by covalently inserting fluorophore molecules in the genome. ATAC-see is compatible with multimodal imaging of landmark proteins, flow cytometry, and enables sophisticated regulome analysis. The compatibility of ATAC-see with fixed samples will allow it to be readily applied to human clinical specimens. The ability to apply ATAC-see in FACS sorting should enhance the dissection of the chromatin basis of cellular heterogeneity. ATAC-see provides rich spatial and epigenomic information that together gives a molecular portrait of the cell. ATAC-see can be used to identify the unique spatial organization of the accessible genome in different human cell types and organs that comprise the human cell atlas, and reveal fine structure of accessible chromatin organization in clinical diagnosis by using super-resolution microscopy. Finally, transposome engineering facilitated the successful combination of imaging and epigenomics; extending this approach may facilitate novel modes of genome interrogation and control.

Materials and Methods

Cell Culture:

GM12878 cells were grown in RPMI 1640 (11875-093, Gibco), 2 mM L-glutamine (25030-081, Gibco), 15% fetal bovine serum (07905, Gibco) and 1% Pen/Strep (15140-122, Gibco). HT1080 cells were cultured in DMEM/F-12, GlutaMAX™ supplement (10565-018, Gibco), 10% fetal bovine serum (07905, Gibco), and 1% Pen/Strep (15140-122, Gibco). HeLa cells were maintained in DMEM (11965-092, Gibco), 10% fetal bovine serum (07905, Gibco), and 1% Pen/Strep (15140-122, Gibco). Neural progenitor cells (NPCs) were cultured in N2B27 media (DMEM/F12, Invitrogen 11320-033; Neurobasal, Gibco 21103-049; NDiff Neuro-2 Medium Supplement Millipore, SCM012; B27 Supplement, Gibco 17504-044) supplemented with EGF and FGF (10 ng/mL each) (315-09 and 100-18B, Peprotech). NPCs were passaged every other day with Accutase (SCR005, Millipore) and seeded on gelatin-coated plates. All cells were kept under standard 37° C. and 5% $CO_2$ conditions.

Human $CD4^+$ T Cells Isolation:

Human $CD4^+$ T cells were isolated from whole blood of healthy donors under a Stanford University IRB-approved protocol. In brief, RosetteSep® Human $CD4^+$ T Cell Enrichment Cocktail was added into the whole blood with a final concentration of 50 μL/mL, and the mixture was incubated 20 min at room temperature. After incubation, the whole blood was diluted with equal volume of PBS+2% FBS (07905, Gibco). Then the diluted samples were layered on top of the density medium and centrifuged for 20 min at 1200×g at room temperature with the brake off. The enriched cells were collected into a new tube and washed with PBS+2% FBS twice. The residual red blood cells are lysed with buffer EL (79217, Qiagen) 5 min at room temperature.

Neutrophil Isolation:

Human neutrophils were isolated from healthy donor's blood following as described under a Stanford University IRB-approved protocol[23]. In brief, 7 ml of heparinized blood was layered on 7 ml Histopaque 1119 (11191-100ML, Sigma Aldrich) in a 15 ml Falcon tube, and the mixture was spun 20 min at 800× g at room temperature. The interphase (lymphocytes and monocytes) was discarded and the granulocyte-rich layer of Histopaque 1119 (diffuse, red phase above RBC pellet) was collected in a new tube. 5 ml of cells were washed with 10 ml of medium (HBSS+), and spun 10 min at 200× g at room temperature. The cells were resuspended in 3 ml DPBS with 0.5% human serum albumin (101-15-50, Lee BioSolutions), and the cell suspension was layered on 10 ml of a discontinuous Percoll gradient (85% to 65% Percoll) and spun 20 min at 800×g at room temperature. The interphase between 70% and 75% Percoll layers were collected in a new 15 ml tube. The tube was added with DPBS with 0.5% human serum albumin up to 15 ml and spun for 10 min at 200× g at room temperature. The cell pellet was resuspended in RPMI-HEPES (10 mM) at $1.5 \times 10^6$ cells per ml for neutrophil activation.

Human Neutrophil Activation:

Human neutrophils were stimulated by Phorbol myristate acetate (PMA) as described[23]. Briefly, the purified neutrophils were suspended in 3 ml RPMI 1640 with final concentration of $1.5 \times 10^6$ per ml in loosen cap 15 ml falcon tube, and incubated in cell culture $CO_2$ incubator (5% $CO_2$, 37° C.) with final concentration of 30 nM PMA for 1 h, 3 h, and 5 h respectively. After 2 h of simulation, protease inhibitor cocktail was added at a 1:200 dilution to both control and simulated tubes. At the respective time points, neutrophils were fixed with 1% formaldehyde for 10 min at room temperature, and fixed neutrophil cells spun down on the glass slide with cytospin 1000 rpm 5 min at room temperature for ATAC-see or immuno-staining.

PAD4 Inhibitor Treatment in Human Neutrophil:

The PAD4 inhibition was performed as previously described[25]. In brief, the isolated human neutrophils were incubated with 200 µM Cl-amidine for 30 min before PMA stimulation.

Hyperactive Tn5 Production:

Hyperactive Tn5 was produced as previously described[30]. In brief, pTXB1-Tn5 plasmid (60240, Addgene,) was introduced into T7 Express LysY/Iq E. coli strain (C3013, NEB). 10 ml of overnight cultured E. coli was inoculated to 500 ml LB medium. After incubation for 1.5 hrs at 37° C., bacteria was incubated about 2.5 hrs at room temperature. When the OD600=0.9, Tn5 protein was induced by adding 0.25 mM IPTG for 4 hrs. E. coli pellet was resuspended in lysis buffer (20 mM HEPES-KOH pH 7.2, 0.8 M NaCl, 1 mM EDTA, 10% glycerol, 0.2% triton X-100, complete proteinase inhibitor (11697498001, Roche)) and lysed by sonication. 10% PEI was added to supernatant of lysate to remove bacterial genomic DNA. 10 ml chitin resin (S6651L, NEB) was added to the supernatant and incubated with rotating for 1 hr at 4° C. The resin washed by lysis buffer extensively. In order to cleave Tn5 protein from intein, lysis buffer containing 100 mM DTT was added to the resin and stored in 4° C. After 48 hrs, protein was eluted by gravity flow and collected in 1 ml fractions. 1 ul of each fraction was added to detergent compatible Bradford assay (23246, ThermoFisher Scientific) and peaked fractions were pooled and dialyzed against 2× dialysis buffer (100 mM HEPE-KOH pH7.2, 0.2 M NaCl, 0.2 mM EDTA, 2 mM DTT, 0.2% triton X-100, 20% glycerol). Dialyzed Tn5 protein was concentrated by using ultracel 30-K column (UFC903024, Millipore) and the quantity of Tn5 was measured by Bradford assay and visualized on NuPAGE Novex 4-12% Bis-Tris gel (NP0321, ThermoFisher Scientific) followed by Coomassie blue staining.

Adaptor Sequences:

The Atto-590N labeled oligonucleotides for Tn5 transposome adaptor were synthesized at INTERGATED DNA TECHNOLOGIES (IDT), and the sequences of oligonucleotide are as follows: Tn5MErev, 5'-[phos]CTGTCTCT-TATACACATCT-3' (SEQ ID NO: 1); Tn5ME-A-ATTO590, 5'-/5ATTO590/TCGTCGGCAGCGTCA-GATGTGTATAAGAGACAG-3' (SEQ ID NO: 2); Tn5ME-B-ATTO590: 5'-/ATTO590/GTCTCGTGGGCTCG-GAGATGTG TATAAGAGACAG-3' (SEQ ID NO: 3).

Tn5 Transposome Assembly:

The assembly of Tn5 transposome was performed as described[30]. Briefly, oligonucleotides (Tn5ME-A-ATTO590, Tn5ME-B-ATTO590, Tn5MErev) were resuspended in water to a final concentration of 100 µM each. Equimolar amounts of Tn5MErev/Tn5ME-A-ATTO590 and Tn5MErev/Tn5ME-B-ATTO590 were mixed in separate 200 µl PCR tubes. These two tubes of oligos mixtures were denatured on a thermocycler for 5 min at 95° C., and cooled down slowly on the thermocycler by turning off the thermocycler. The Tn5 transposome was assembled with the following components: 0.25 vol Tn5MErev/Tn5ME-A-ATTO590+Tn5MErev/Tn5ME-B-ATTO590 (final concentration of each double strand oligo is now 50 µM each), 0.4 vol glycerol (100% solution), 0.12 vol 2× dialysis buffer (100 mM HEPES-KOH at pH 7.2, 0.2 M NaCl, 0.2 mM EDTA, 2 mM DTT, 0.2% Triton X-100, 20% glycerol), 0.1 vol SL-Tn5 (50 µM), 0.13 vol water. The reagents were mixed thoroughly but gently and the solution was left on the bench at room temperature for 1 h to allow annealing of oligos to Tn5.

Slide Preparation and Fixation:

HT1080 cells and HeLa cells were grown on secureSlip cell culture system (0515073, GRACE BIO-LABS) until 80-90% confluent and fixed with 1% formaldehyde (Sigma-Aldrich) for 10 min at room temperature. GM12878 cells were fixed with 1% formaldehyde (Sigma) 10 min at room temperature and centrifuged on the glass slide with Cytospin, 1000 rpm for 5 min, 30-50,000 cells per slide.

Immuno-Staining:

The formaldehyde fixed slide was rinsed in PBS and permeabilized in PBS 0.5% Triton-X 100 for 10 mins at room temperature. Then, the slide was blocked with antibody dilution reagent (00-3218, ThermoFisher Scientific) for 1 h at room temperature. Primary antibodies were diluted in antibody dilution reagent 1:500: (rabbit anti-LaminB1 (ab16048, Abcam), mouse anti-mitochondria (ab3298, Abcam), and Anti-Cyclin E1 antibody [EP435E] (Alexa Fluor® 488) (ab194068, Abcam), rabbit anti-H3K9 me3 (SAB4800027-100UL, Sigma), rabbit anti-H3K9 me2 (39375, Active Motif), rabbit anti H3K27acetylation (25238, BPS Bioscience), rabbit anti-H3 citrulline (ab5103, Abcam), mouse anti-Phospho RNA Polymerase II CTD (Ser5) mAb (MABI0603, MBL International), and incubated overnight at 4° C. After washing with PBS containing 0.05% Tween-20 for 3 times 10 min each, slides were incubated with secondary antibodies goat anti-rabbit-ATTO488 (18772-1ML-F, Sigma-Aldrich) or goat anti-mouse-Atto647N (50185-1ML-F, Sigma-Aldrich), for 45 min at room temperature. The slides were washed with PBS containing 0.05% Tween-20 for 3 times 10 min each, mounted using Vectashield with DAPI (H-1200, Vector labs) and imaged with Leica SP8 or Zeiss LSM 700.

For ATAC-see co-staining with epigenetic marks or RNAP II, the ATAC-see was performed first and then immune-staining was done on the same slide. All the primary antibodies was diluted in 1:500 ratio, and the antibodies information as follows: rabbit anti-H3K9 me3 (SAB4800027-100UL, Sigma); rabbit anti-H3K4 me3 (ab8580, Abcam); rabbit anti H3K27acetylation (25238, BPS Bioscience); mouse anti-Phospho RNA Polymerase II CTD (Ser5) mAb (MABI0603, MBL International); mouse anti-H3K27 me3 (ab6147, Abcam); rabbit anti-RNA polymerase II CTD (Ser-5) antibody (ab5095, Abcam).

ATAC-see: After fixation, the cells (either growing on slide or centrifuged on glass slide with cytospin) were permeabilized with lysis buffer (10 mM Tris-Cl, pH 7.4, 10 mM NaCl, 3 mM MgCl2, 0.01% Igepal CA-630) for 10 min at room temperature. After the permeabilization, the slides were rinsed in PBS twice, and put in humid chamber box at 37° C. The transposase mixture solution (25 µl 2× TD buffer, final concentration of 100 nM Tn5-ATTO-59ON, adding dH2O up to 50 µl) was added on the slide and incubated for 30 min at 37° C. After the transpose reaction, slides were washed with PBS 0.01% SDS for 15 min 3 times at 55° C. After washing, slides were mounted using Vectashield with DAPI (H-1200, Vector labs) for imaging with Leica SP8 or Zeiss 700 or for additional co-staining with Lamin B1 or mitochondria (see the materials and methods above).

ATAC-See with XIST RNA FISH:

Female mouse neural progenitor cells (NPCs) were grown on secureSlip cell culture system (0515073, GRACE BIO-LABS) until 80-90% confluent and fixed with 1% formaldehyde (Sigma-Aldrich) for 10 min at RT. After washed with PBS three time (5 mins each), the slide was permeabilized with PBS 0.1% NP-40 10 mins at RT. ATAC-see (with Atto-480 labeled Tn5) were performed under standard protocol as stated above. After the ATAC-see, the slide was dehydrate in 70% EtOH for 1 hr at 4° C., and re-hydrated in 2×SSC+10% formamide for 5 mins at RT. The XIST RNA FISH probes (Stellaris mXist) were hybridized on the slide overnight at 37° C. The washing was conducted in following conditions: 2×30 mins in 2×SSC+10% formamide at 37° C. and 5 mins in 2×SSC at 37° C. After RNA FISH washing, the slide were mounted with Vectashield (H-1200, Vector labs).

FACS Sorting and Analyzing of ATAC-See:

GM12878 cells were washed with PBS, then fixed with 1% formaldehyde for 10 min at room temperature. After the fixation, cells were permeabilized with lysis buffer (10 mM Tris-Cl, pH 7.4, 10 mM NaCl, 3 mM MgCl2, 0.01% Igepal CA-630) and centrifuged at 700 g for 10 min at room temperature. $5 \times 10^6$ cells were then either stained with DAPI (for negative control), or transposed for 30 min at 37° C. using Atto-594 labeled in-houseTn5 (see materials and methods above). After transpose reaction, cells were centrifuged and stained with DAPI, analyzed and sorted using a BD FACS-Aria II (BD Biosciences). Collected G1 high, G1 low, S and G2 were reverse crosslinking, purified and amplified by standard ATAC-seq PCR reaction, and the libraries were sequenced on Illumina NextSeq at the Stanford Functional Genomics Facility. The sorted ATAC-See different groups were collected on glass slide using Cytospin, and images were taken under Zeiss 700. The sorted ATAC-See G1 high and G1 low cells were collected and centrifuged by using Cytospin, and Anti-Cyclin E1 antibody [EP435E] (Alexa Fluor® 488) (ab194068, Abcam) were stained on different groups. For bone marrow progenitor studies, cells were harvested from femur, tibia, and humerus. Bones were fragmented by mortar and pestle, and debris was removed by gradient centrifugation using Histopaque 1119 (Sigma-Aldrich). Cells were passed through a 70-uM strainer, and red blood cells were lysed with ACK lysis buffer. 5-10×10^6 cells were stained at 4° C. in FACS buffer (DPBS+0.5% BSA+2 mm EDTA) with the following antibodies at a 1:200 dilution: CD16/32 eFluor450 (93, eBioscience), CD117 FITC (2B8, eBioscience), CD11b-redFluor710 or APC (M1/70, Tonbo Bioscience), B220-PE (RA3-6B2, eBioscience), and CD105-PE (MJ7/18, eBioscience). Cells were then washed, fixed, and transposed as described above. CMPs were identified as Lineage$^c$ kit$^h$-,CD16/32$^-$. GMPs were identified as Lineage$^-$ ckit$^{hi}$CD16/32$^+$. Band neutrophils were identified as Lineage$^-$ckit$^-$CD11b$^+$ CD16/32$^+$. Cells were sorted into FACS buffer, and cell purities of at least 95% were confirmed by post-sort analysis.

Atac-Seq:

ATAC-seq with Illumina Tn5 transposase (Nextera) and Atto-590 labeled homemade Tn5 in human GM-12878 cells was performed as described[3]. Briefly, 50,000 cells were centrifuged 500 g 5 min at room temperature. The cell pellet was resuspended in 50 µl lysis buffer (10 mM Tris-Cl, pH 7.4, 10 mM NaCl, 3 mM MgCl2, 0.01% Igepal CA-630) and centrifuged immediately 500 g for 10 min at 4° C. The cell pellet was resuspended in 50 µl transposase mixture (25 µl 2× TD buffer, 22.5 µl dH2O and 2.5 µl Illumina Tn5 transposase or with final concentration of 100 nM Atto-590 labeled in-houseTn5) and incubated at 37° C. 30 min. After transposition, the mixture was purified with Qiagen Mini-purification kit and eluted in 10 µl Qiagen EB elution buffer. Sequencing libraries were prepared following the original ATAC-seq protocol[3]. The sequencing was performed on Illumina NextSeq at the Stanford Functional Genomics Facility.

ATAC-Seq in Fixed Cells:

Human HT1080 cells were fixed with 1% formaldehyde (Sigma, USA) for 10 min and quenched with 0.125 M glycine for 5 min at room temperature. After the fixation, cells were counted and 50,000 cells were used per ATAC-seq reaction. The transposed reaction is same as normal ATAC-seq except with 0.05% Igepal CA-630 in the lysis buffer. After the transposase reaction, a reverse crosslink solution was added (with final concentration of 50 mM Tris-Cl, 1 mM EDTA, 1% SDS, 0.2M NaCl, 5 ng/ml proteinase K) up to 200 µl. The mixture was incubated at 65° C. with 1000 rpm shaking in a heat block overnight, then purified with Qiagen Mini-purification kit and eluted in 10 µl Quiagen EB elution buffer. Sequencing libraries were prepared following the original ATAC-seq protocol[3]. The sequencing was performed on Illumina NextSeq at the Stanford Functional Genomics Facility.

ATAC-Seq after Imaging:

80% confluent Human HT1080 cells (30-50,000 cells) grown in 8 well chamber slides were fixed with 1% formaldehyde (Sigma, USA) for 10 min and quenched with 0.125 M glycine for 5 min at room temperature. After fixation, slides were put in PBS at 4° C. Cells on slides were permeabilized with lysis buffer (10 mM Tris-Cl, pH 7.4, 10 mM NaCl, 3 mM MgCl2, 0.05% Igepal CA-630) for 10 min. The 50 µl transposase reaction solution was added onto the slide, and the cells on slide were incubated at 37° C. for 30 min. For the imaging and sequencing, slides were mounted using Vectorshield and images were taken with a Zeiss LSM 700. After imaging, the coverslip was removed and cells were lysed with 50 µl of 50 mM Tris-Cl, 1 mM EDTA, 1% SDS, 0.2 M NaCl 5 min on slide at room temperature. The cell lysis was carefully transferred to 1.5 ml eppendorf tube. The glass slide was washed with 50 µl of the same buffer another 3 times and washing solutions were transferred to the same tube carefully. After adding final concentration of 50 µg/µl proteinase K to the cell lysate, the mixture was incubated at 65° C. with 1000 rpm shaking in a heat block overnight, purified with Qiagen Mini-purification kit and eluted in 10 µl Qiagen EB elution buffer. Sequencing libraries were prepared following the original ATAC-seq protocol[3]. The sequencing was performed on Illumina NextSeq at the Stanford Functional Genomics Facility. For ATAC-seq after imaging the human neutrophils, 50,000 cells were centrifuged on the glass slides with cytospin. The remaining steps are same as for HT1080 cells except the lysis buffer contains 0.01% Igepal CA-630.

For the systematically sensitivity assay of ATAC-seq after imaging, different amount of cells (50000, 5000, 500, and 50 cells) were seed in the 8 well chamber with duplications, and cells were fixed as stated above after 6 h seeding. The following procedures are same as stated above.

DNA FISH Probe Labeling:

DNA FISH probes labeling was performed as previous described[31]. In brief, BAC clones (ThermoFisher Scientific), RP11-626N18, RP11-832P24, RP1163J14, RP11637D5, RP11-368K11, RP11-116A9, were cultured based on standard protocol and purified with BACMAX™ DNA Purification Kit (BMAX044, Epicenter). After the purification, BACs were sheared to 300-800 bp with sonication. The sheared BAC DNA was labeled with BioPrime® Array CGH Genomic Labeling System (18095-011, Thermo Fisher scientific) by mixing with either Cy3-dCTP (RP11-626N18, RP1163J14) (PA53021, GE healthcare life science, USA), Green 496 dUTP (RP11-832P24, RP11637D5) (ENZ-42831L-0050, Enzo life science) or Cy5-dCTP (RP11-368K11, RP11-116A9) (PA55021, GE healthcare life science) respectively. The labeled probes were purified with MinElute PCR Purification Kit (28006, Qiagen).

DNA FISH in Human Neutrophil:

DNA FISH was done as previously described[31]. In brief, purified human neutrophils were fixed with 1% formaldehyde for 10 min at room temperature, centrifuged on glass slides with cytospin and stored in 70% ethanol. The neutrophils on slides were permeabilized in PBS 0.5% Triton-x 100 for 10 min at room temperature, rinsed in PBS, denatured in 2×SSC/50% formamide for 30 min at 80° C., and put in ice cold 2×SSC for 5 min. At the same time, 40 µl of hybridization mixture, 100 ng BAC probes, 1×DNA FISH hybridization buffer (2×SSC, 10% dextran sulfate, 50% formamide), at a final concentration of 100 ng/µl human Cot-1 DNA (15279-011, Thermo Fisher scientific), was denatured for 5 min at 95° C. and put on ice for 5 min. After adding denatured probes onto the denatured neutrophils on slide, the slide was hybridized in a humid dark box for 14 h at 37° C. On the second day, the slide was sequentially washed twice in 2×SSC/50% formamide for 15 min at 40° C. and twice with 2×SSC for 15 min at 40° C. After washing, the slide was mounted using Vectashield with DAPI (H-1200, Vector labs). 3D DNA FISH images were taken with Zeiss LSM 700. The distance between the center of DNA FISH signal and edge of DAPI staining were manually measured in Volocity (Perkin Elmer), and on the nucleus periphery was defined by distance less than 0.1 µm.

Imaging Processing for ATAC-See Signal:

Cell nuclei were identified and segmented by Gaussian filtering raw DAPI image data, and then applying an intensity threshold to generate nuclear outlines. Nuclei were randomly selected, and over ~30 nuclei were chosen for each cell line. All nuclear outlines were verified by eye. Regions of the cell containing mitochondria were excluded from all analysis using a mitochondrial mask, similarly generated by gaussian filtering Mito-Tracker image data, and applying an intensity threshold.

Correlations between DAPI and ATAC-see signals were measured on a per-pixel basis within the nucleus, with each channel normalized to its mean intensity per nucleus. Correlation data was fit to a linear regression on both a per-cell basis, and a cell population basis. Intensity distributions of DAPI and ATAC-see signals were measured as a function of radial distance from the nuclear rim toward the nuclear center by measuring the average intensity within a series of 1 pixel wide annuli generated through iterative erosion of each nuclear outline. Each channel was again normalized to its mean intensity per nucleus.

Bright regions of ATAC-see signal within each nucleus were identified by Gaussian filtering the raw data, and then thresholding to find all regions more than 50% brighter than the mean filtered intensity. The fraction of area within a bright region was calculated per cell as the total bright spot area over the total nuclear area. All analysis was performed using a custom-written python and C++ code, drawing heavily on NumPy and SciPy.

Signal intensity measurement was performed in Volocity software (PerkinElmer), and the signal intensity correlation of ATAC-see and other marks (including H3K4 me3, H3K27Ac, H3K9 me3, H3K27 me3, RNAPII ser-2, RNAPII ser-5) or XIST RNA-FISH was calculated by Volocity software by using DAPI staining as mask and plot in custom written R script.

ATAC-Seq Library Data Preprocessing:

ATAC-seq paired-end reads were trimmed for Illumina adapter sequences and transposase sequences using an in-house script and mapped to hg19 using Bowtie2[32] v2.1.0 with parameters—very sensitive. Over ~11 million mapped reads were generated in each sequencing library and used for downstream data mining, and there are over ~35 million mapped reads in each sequencing library from human neutrophil and NETosis. Duplicate reads were removed with Picard (http://picard.sourceforge.net) v1.79. Peak calling was performed by MACS2[33] narrow peak mode with parameters—q 0.01—nomodel—shift 0. Overlapping peaks from all samples were merged together to a consensus peak list, and number of unique and properly paired reads mapped to each peak for each individual samples was quantified to calculate the Pearson Correlation. The insert size of fragments was estimated from the distance between the pair-ended reads, and plotted against the frequency in a histogram. Genome Ontology Enrichment Analysis was performed in GREAT software[34]. EdgeR was used to identify variable peaks between Atto-Tn5 vs Nextera, and between technical replicates from either Atto-Tn5 and Nextera.

ATAC-Seq Signal Intensity Around TSS:

A 2 kb window centered on TSS was divided into 40 equal sized bins of 50 bp. The number of unique-mapped and properly paired ATAC-Seq tags overlapping each bin was counted. The average fragment count plotted in each bin was normalized to total 10 millions of reads.

ATAC-Seq Signal Intensity Around LADs:

The human Lamin Associated Domains (LADs) were downloaded. All 1,302 LADs were aligned by their left or right border and calculated average profiles of ATAC-Seq read coverage across the combined 2,604 borders. In detail, a 200 kb window centered on 2,604 LAD borders was divided into 40 equal sized bins of 50 kb. The order of the bins for the right borders of LADs is the reverse of that for the left borders. The number of unique-mapped and properly paired ATAC-seq tags was counted in each bin. The average fragment count plotted in each bin was normalized to total 10 millions of reads. To compare the ATAC-seq signal inside and outside LADs, 10 kb non-overlapping sliding windows on the human genome were taken, and calculated ATAC-Seq read counts in each window. The windows were labeled inside the LADs as 1 and outside the LADs as 0, and then plotted ATAC-seq signals in two groups in a boxplot. T-test was applied to compare the mean of the two groups.

Differential Analysis of ATAC-Seq Peak:

Differentially accessible peaks from the union peak list were identified with edgeR[35] using raw counts of each sample in the overlapping peak list. edgeR was run with default settings, with a fold change threshold of 2, and FDR<0.05. The distribution of differential peaks on the human genome were further investigated using a functional genomic annotation based on 15 chromHMM states[36] derived from ENCODE histone markers on the GM12878 cell line.

REFERENCES FOR MATERIALS AND METHODS

30. Picelli et al. *Genome research* 24, 2033-2040 (2014).
31. Chen et al. *Biotechniques* 56, 117-+(2014).
32. Langmead et al. *Genome biology* 10, R25 (2009).
33. Zhang et al. *Genome biology* 9, R137 (2008).
34. McLean et al. *Nature biotechnology* 28, 495-501 (2010).
35. Robinson et al. *Bioinformatics* 26, 139-140 (2010).
36. Ernst et al. *Nature methods* 9, 215-216 (2012).

Example 1

ATAC-See for Regulatory DNA Imaging and Sequencing

A bifunctional Tn5 transposome with fluorescent adaptors was designed, produced, and optimized. Recombinant purified hyperactive Tn5 transposase loaded with Atto590 fluorophore-conjugated adaptors (Atto-Tn5) retained the activity and selectivity of the standard unlabeled Tn5 transposome (Nextera Tn5) (FIG. 1, panels b, c). ATAC-seq of human B-cells (GM12878) showed the DNA accessibility profile generated with Atto-Tn5 is highly correlated with that obtained using Nextera Tn5 (R=0.96) (FIG. 1 panel c). Moreover, standard quality control metrics such as DNA insert length distribution, transcriptional start site (TSS) enrichment, and genomic distribution of ATAC-seq peaks, were also very similar among Atto-Tn5, Nextera Tn5, and published ATAC-seq data from the same cell line[3] (FIG. 1 panel c). Comparison of Atto-Tn5 vs. Nextera Tn5 showed no greater variation than between technical replicates of Nextera Tn5, suggesting that the bifunctional Tn5 transposome bearing molecular tags does not affect transposase activity. Our labeling strategy is general and compatible with different fluorophores and other chemical tags (data not shown).

Methods to perform ATAC-seq in crosslinked samples were developed because cellular fixation is a common and essential step to preserve nuclear architecture and cellular composition. Transposition of formaldehyde fixed cells produced biased libraries with short DNA fragments[3]. A reverse crosslinking method compatible with ATAC-seq was developed. ATAC-seq data from fixed HT1080 fibrosarcoma cells in this manner is comparable to standard ATAC-seq from living cells (R=0.93) (FIG. 1 panel d), indicating fixation condition does not affect the Tn5 tagmentation efficiency in the intact nucleus. The capacity to engineer the transposome to label accessible DNA in fixed samples sets the stage for sequentially imaging and sequencing the accessible genome.

Figure 2:
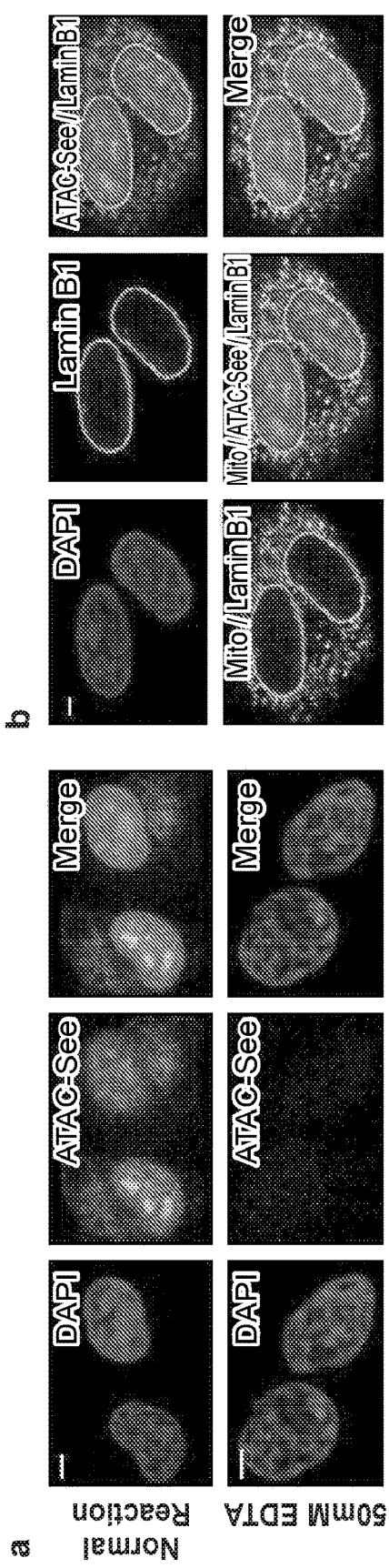
FIG. 2: ATAC-see enables imaging and sequencing the accessible genome in the same cells. Panel a, Representative image of ATAC-see result in HT1080 cells. Very limited ATAC-see signal is observed in +EDTA negative control. Scale bar=2 µm. Panel b, Multimodal imaging combining ATAC-see with immunofluoreseence. The representative images show outside of nucleus ATAC-see signals are overlapping with mitochondria by co-staining with nucleus Lamin B1 and mitochondria protein marker (Mito). Scale bar=2 µm. Panel c, Genomic tracks of ATAC-seq data from standard protocol and Atto-Tn5 on slide after imaging. X-axis is genomic coordinates; Y-axis is normalized ATAC-seq read counts. Panel d, Genome-wide comparisons of standard ATAC-seq data and Atto-Tn5 on slide after imaging. Left: Scatter plot of all data points. Right: Metagene analysis centered on transcriptional start sites (TSS).
Figure 2:
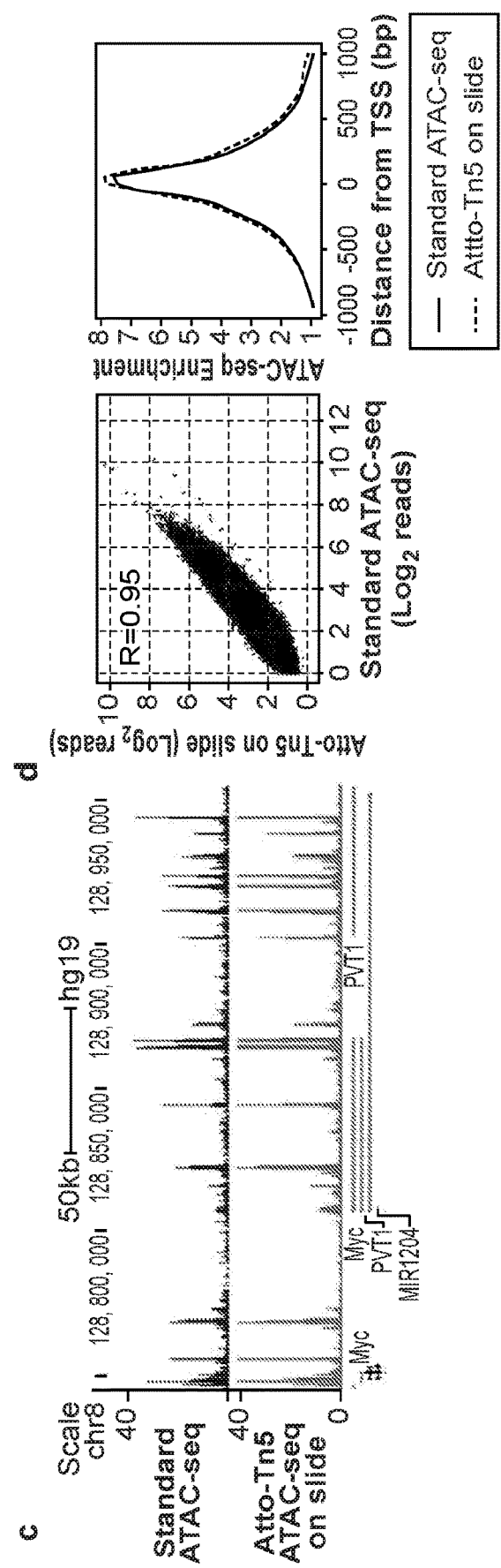

ATAC-see experiments revealed the three dimensional spatial organization of accessible DNA in situ. Adherent HT1080 cells were fixed by formaldehyde per standard immunofluorescence (IF) on glass slides, and reacted with Atto-Tn5. Samples were then stringently washed, counterstained for total DNA by DAPI (4',6-diamidino-2-phenylindole), and imaged with confocal microscopy. The images showed that the accessible chromatin is heterogeneously distributed throughout the nucleus and distinct from DAPI signal (which demarcates tightly packed DNA). ATAC-see signal was concentrated into several nuclear foci in some but not all cells (FIG. 2 panel a). This result suggests that the accessible genome forms higher order structure in the intact nucleus; these foci of accessible genome may reflect the open-chromatin rich "A compartment" detected by chromosome conformation capture techniques[6]. Addition of 50 mM EDTA that inactivates Tn5 activity[3, 9-11] greatly reduced the ATAC-see signal to 2.69%±0.04% of control (FIG. 2 panel a). Thus, the ATAC-see signal reflects the integration of fluorophore-labeled adaptors into accessible genomic DNA.

Conditions for multimodal labeling and imaging with ATAC-see were developed. ATAC-seq is known to capture mitochondria DNA (which is not chromatinized). Four color imaging combining ATAC-see, DAPI, and IF of lamin B1 and a mitochondrial protein marker clearly delineated the nuclear accessible genome, and revealed a strong overlap between mitochondria and ATAC-see signal outside of nucleus (FIG. 2 panel b). Combined ATAC-see and IF with 4 histone marks and 2 forms of RNA polymerase II (RNAPII ser-2 and ser-5 phosphorylation) showed strong co-localization of ATAC-see in nuclear territories with active marks H3K4 me3, H3K27ac and RNAPII (R~0.80), but absent or negative correlation with repressive marks H3K27 me3 and H3K9 me3 (R=0 to −0.20). To further confirm that ATAC-see specifically labeling accessible chromatin, ATAC-see was combined with Xist RNA FISH, which marks the inactive X chromosome, in female cells. It was found that the Xist RNA cloud lies within an ATAC-see poor "hole", with 2.3±0.14 fold lower ATAC-see signal within than outside the Xist domain (p<0.005). These results validate the specificity of ATAC-see in localizing active regulatory elements and, by exclusion, heterochromatin in the nucleus. The ability to combine ATAC-see with the extensive toolkits of IF imaging suggests facile adoption and ability to broadly impact broad range of biomedicine.

To perform sequencing after imaging, an on-slide lysis procedure compatible with ATAC-see samples was developed. ATAC-seq data after ATAC-see imaging of the same sample is highly correlated with standard ATAC-seq of parallel cell samples (R=0.95; FIG. 2 panels c, d). In addition, differential peaks analysis of ATAC-seq peaks shows the variation between Atto-Tn5 and Nextera Tn5 is no greater than the variation between technical replicates of Nextera Tn5. On-slide and fixed ATAC-see with serial cell dilution showed highly reproducible mapping of DNA accessibility with input ranging from 50,000 to 500 cells. Sequential imaging and accurate mapping of the open chromatin landscape by sequencing suggest that ATAC-see captures a comprehensive portrait of the spatial organization of the accessible genome.

Example 2

Cell Type-Specific Spatial Organization of the Accessible Genome

Figure 3:
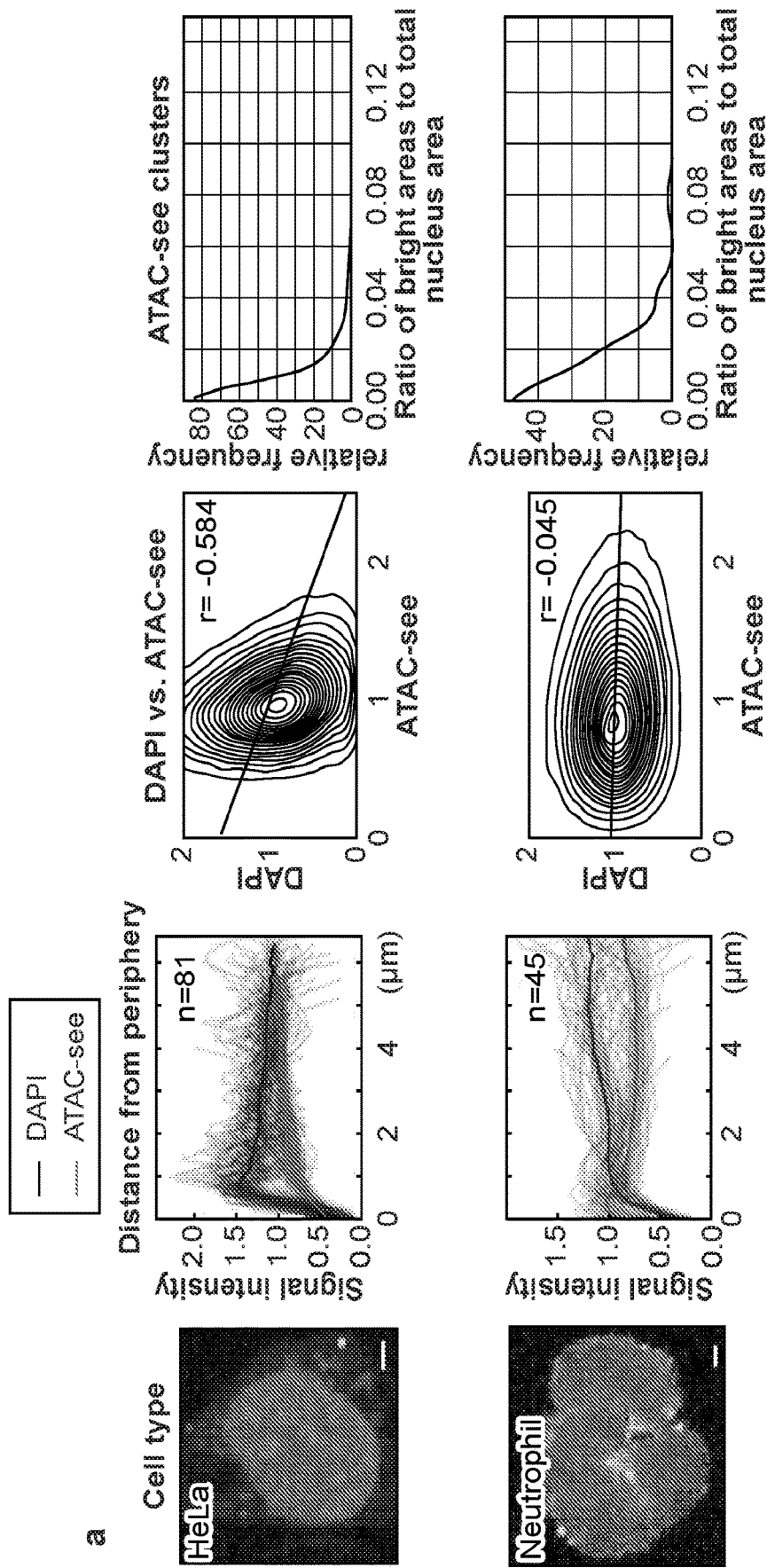
FIG. 3: Cell type specific accessible chromatin organization in the intact nucleus. Panel a, Image analysis. For each cell type (organized in rows), the following is displayed from left to right columns: (i) A representative ATAC-see image (red color is ATAC-see and blue is DAPI, scale bar=2 µm). (ii) Signal intensity of ATAC-see and DAPI as a function of distance from nuclear periphery. Each trace is one nucleus; n=number of nuclei analyzed. (iii) Correlation of ATAC-see and DAPI signal intensity; Pearson correlation (r) is indicated. (iv) ATAC-see clusters, quantified as the ratio of ATAC-see bright areas vs total nucleus area. Panel b, Unique feature of ATAC-seq from human neutrophil (Neuts) after imaging. Left: Genome browser track of ATAC-seq in human neutrophil, H3K27Ac layer from ENCODE 7 cell lines, and NKI Lamin associated domains (LADs). X-axis is genomic coordinates; Y-axis is ATAC-seq normalized read counts. The grey square indicates the location of BAC chosen for DNA FISH in c. Right: Metagene plot of human neutrophil ATAC-seq signal centered on the boundary between NKI LADs and neighboring sequences. Panel c, Left: example of DNA FISH from indicated BAC (in b) in human neutrophil, and the arrow indicates the FISH signal at the neutrophil periphery; Right: Location quantification of DNA FISH signal from the indicated BACs in the human neutriophil. At the nucleus periphery was defined by distance between DNA FISH signal to DAPI staining edge less than 0.1 µm (see method). n=alleles number counted in DNA FISH. P-values were calculated by a binomial test.
Figure 3:
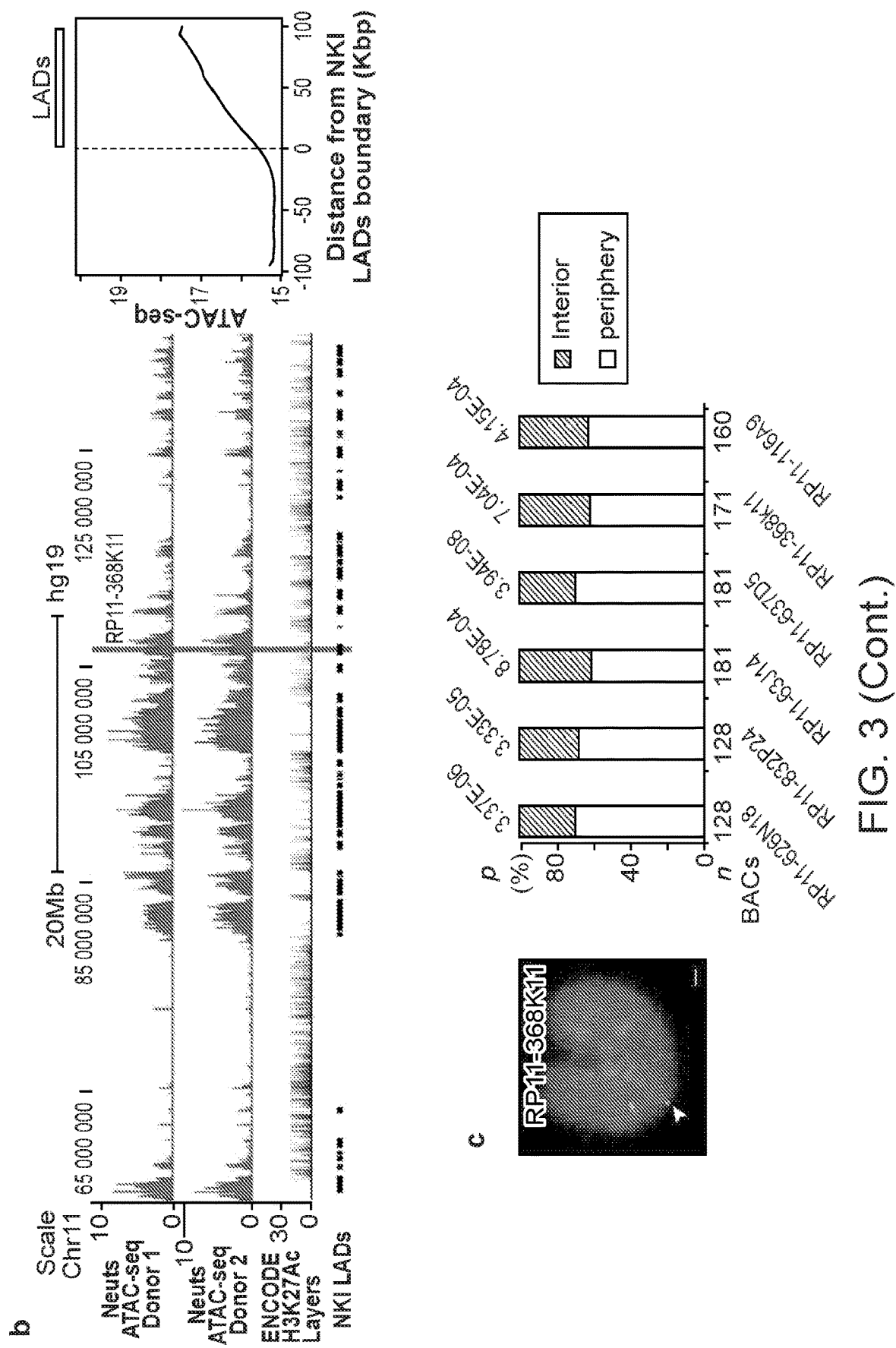

ATAC-see of five human cell types revealed that chromatin accessibility is spatially organized in a cell type-specific fashion with overlaid single cell variation (FIG. 3 panel a). Nuclear architecture is hierarchically organized into distinct compartments, topological domains, and chromosome loops[1, 14]. Heterochromatin is believed to be physically condensed, DAPI-avid, and typically resides near the nuclear periphery[15]. In contrast, euchromatin contains accessible regulatory elements and active genes, and tends to be located in the nuclear interior[1, 10, 16]. It is possible that ATAC-see signal would be more prominent in nuclear interior and be anti-correlated with the DAPI signal in individual nuclei. Mitochondrial contribution to ATAC-see signal was masked out. In HeLa cells, ATAC-see signal indeed increases gradually from the nucleus periphery to the interior, and is inversely correlated with DAPI staining (R=−0.584, FIG. 3 panel a). However, analyses of additional cell types with the same strategy showed multiple exceptions to this simplistic picture. Primary human $CD4^+$ T cells exhibited lower anti-correlation between ATAC-see and DAPI signal (R=−0.243), and the intranuclear distribution of the ATAC-see signal varied dramatically from cell to cell. In addition, some but not all of CD4+ T cells had a cruciform pattern of clustered foci of ATAC-see signal. Approximately 40% of CD4+ T cells had a strong ATAC-see at the nuclear periphery in a semi-circular "cap pattern". B-lymphoblastoid GM12878 cells also exhibited single cell ATAC-see variation, but lacked intranuclear clusters of ATAC-see foci. In contrast, adherent HT1080 fibrosarcoma cells more closely resembled HeLa cells in the segregation of DAPI-rich heterochromatin to the nuclear periphery and ATAC-see to nuclear interior, with the notable distinction of prominent nuclear clusters of ATAC-see foci.

Neutrophils are abundant immune cells that play important roles in infection control and in inflammation[18]; they also have distinctive multi-lobulated nuclei. ATAC-see of primary human neutrophils revealed a striking and unique organization of the accessible genome—the vast majority of the ATAC-see signal in neutrophils is located at the nucleus periphery to form a rim structure (FIG. 3 panel a. Neutrophil ATAC-see signal intensity decreases from the nuclear periphery to interior, and there is little correlation between ATAC-see and DAPI signals (R=−0.045). The rim pattern of ATAC-see signal is not due to mitochondria, as evidenced by the distinct staining pattern of a mitochondrial marker in the same cells. ATAC-seq of the same samples after imaging confirmed that greater than 99% of ATAC-see signal arise from genomic DNA. In addition, neutrophils have ~50-fold fewer focal peaks of chromatin accessibility than other cell types with similar sequencing depth and alignment rates[19]. Instead, neutrophils harbor large multi-kilobase blocks of accessible chromatin that are inversely correlated with H3K27Ac from 7 ENCODE cell lines, but are significantly correlated with lamina-associated domain (LADs) (R=0.31 genome-wide, p<0.0001, FIG. 3 panel b)[20]. DNA fluorescent in situ hybridization (FISH) validated that six of six genomic loci indicated by ATAC-see are at the nuclear periphery in neutrophils (FIG. 3 panel c).

The significant correlation between LADs in other cell types and ATAC-seq reads in neutrophils suggests the LADs in the neutrophil are now made accessible. Imaging showed that primary human neutrophils down regulate Lamin B1 protein concomitantly with placement of the accessible genome at the nuclear periphery. Our results also suggest that lamin B lis not required for the peripheral localization of LADs, consistent with another study[21]. Next it was tested whether neutrophil invert their nuclear architecture as in the rod photoreceptor cells[22], however, the spatial distribution of euchromatic marks and heterochromatic marks were localized in the expected pattern in neutrophil nuclei. Thus, human neutrophils have significant transposase-accessible DNA at the nuclear periphery but this accessible DNA does not bear the standard euchromatic marks. Collectively, these observations suggest that distinct human cell types often have a distinctive and diverse spatial organization of the accessible genome (FIG. 3a), typified by human neutrophils.

Example 3

ATAC-See Uncovers the Chromatin Dynamics of NETosis

How the unusual spatial organization of the accessible genome in neutrophils might facilitate neutrophil functions was explored. When a mature neutrophil encounters bacteria in blood or tissue, neutrophils can release their chromatin and kill bacteria, an unique form of programmed cell death termed neutrophil extracellular traps (NETosis)[23]. NETosis is also believed to contribute to human inflammatory diseases, but it is not known whether the genome is randomly fragmented or processed in an organized manner for NET release. It was reasoned that prepositioning of open DNA at the nuclear periphery may prepare neutrophils for initiation of NETosis. Molecular imaging and epigenomic sequencing by ATAC-see and ATAC-seq of the same cells were combined and discovered two key steps in NETosis (FIG. 4).

First, upon neutrophil activation, the LADs located at nuclear periphery serve as focal points for chromatin disassembly into mononucleosomes. Primary neutrophils were stimulated with phorbol myristate acetate (PMA) to trigger NETosis[25] for 1, 3, and 5 hrs. At 1 hr, ATAC-see reveals that the accessible genome is now fragmented into coarse granules, and extends into the nuclear interior (FIG. 4 panel a). ATAC-seq of the same cells showed a gain of chromatin accessibility at genomic loci adjacent to LADs that were previously closed; these accessible sites are predominantly in the form of mononucleosomes (FIG. 4 panel b). Thus, NETosis initiates with a major reorganization of chromatin accessibility around LADs, and spreads from nuclear periphery to the remainder of the genome.

Second, with sustained neutrophil activation, mononucleosomes are further disassembled into free DNA and histones, a step that requires histone citrullination. After 3 hrs of PMA stimulation, approximately half of the neutrophils (49.7%) have released their chromatin into the extracellular space. The NETs have broad ATAC-see signal and contain multiple bright foci, consistent with decondensed chromatin. ATAC-seq of the same samples indicates that the entire genome is accessible, and NETs are largely in the form of free DNA, essentially indistinguishable from the read length distribution of purified genomic $DNA^{3, 10}$. This state remains after 5 hrs of PMA stimulation, and 59.7% of neutrophils have released NETs (FIG. 4 panels a, b). Histone citrullination by PAD4 enzyme has been reported to mediate NETosis and chromatin decondensation[26, 27]. Concurrent treatment of neutrophils with PAD4 inhibitor Cl-amidine (PAD4i) and PMA inhibited histone citrullination and NETosis. PAD4i-treated active neutrophils initiate the gain in chromatin accessibility around LADs and process the chromatin to mononucleosomes, but fail to release free DNA from mononucleosomes even after 5 hrs of neutrophil activation (FIG. 4 panels a, b). Morphologic and genomic analyses indicate that PAD4i-treated cells are arrested at a step between 1 and 3 hrs of neutrophil activation (FIG. panels a, b). Thus, NETosis is separable into two distinct steps, and PAD4-mediated histone citrullination is only required in the second step for disassembling nucleosomes to release DNA as NETs.

Figure 4:
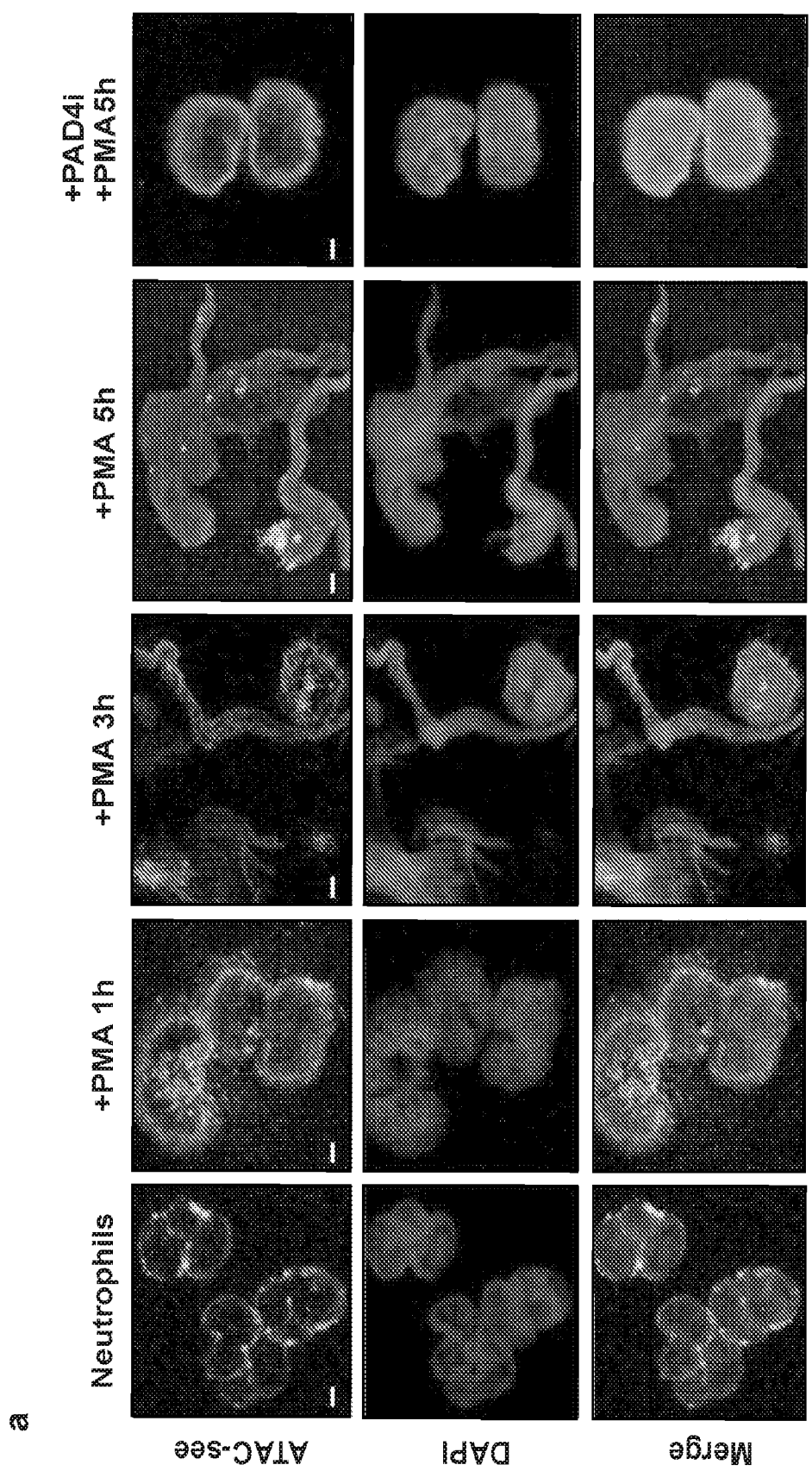
FIG. 4: ATAC-see and -seq reveal the dynamic chromatin organization during human NETosis. Panel a, Representative images ATAC-see in the indicated conditions. PMA stimulation time course, PAD4 inhibitor treatment (PAD4i). Scale bar=2 µm. Panel b, Epigenomic landscape of NETosis. Left column: Genomic tracks of ATAC-seq data from the indicated conditions. Locations of NKI Lamin associated domains (LADs) are indicated. X-axis is genomic coordinates; Y-axis is ATAC-seq normalized read counts. Middle: Metagene plot of ATAC-seq signal centered on the boundary between NKI LADs and neighboring sequences. The top plot is the same as FIG. 3b right panel and is reproduced here for clarity as the baseline in this time course. Right: ATAC-seq insert size distribution for the corresponding samples. Diagnostic insert sizes for accessible DNA, mononucleosome, and di-nucleosome are labeled. Panel c, Proposed model of NETosis illustrates the coordinated dynamics of nuclear architecture, accessible genome reorganization, and genome disassembly.
Figure 4:
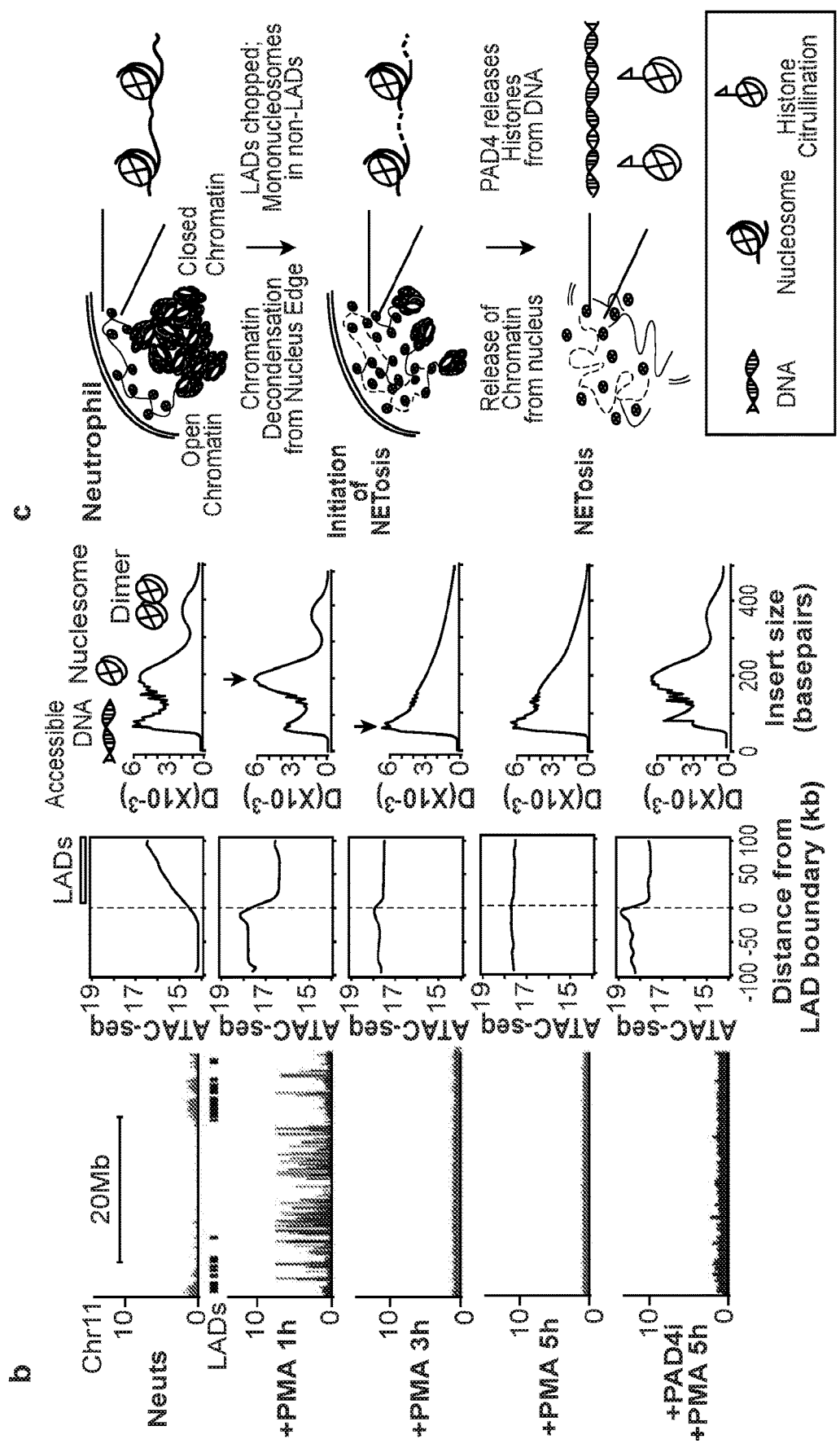

These results show that NETosis is a programmed genome disassembly that is precisely spatially organized and sequence programmed (FIG. 4 panel c). NETosis occurs outside-in, proceeding from the edge to the interior of the nucleus. Chromatin accessibility of LADs, situated at the nuclear periphery, serve as the initial trigger point to process chromatin to nucleosomes, and then histone citrullination disassembles DNA from histones. The ability to image and sequence the accessible genome of the same cells ("see and seq") greatly facilitated our ability to decipher the spatial choreography of this unique form of programmed cell death.

Example 4

ATAC-See with Flow Cytometry Deconvolute Cells by Chromatin Accessibility

Figure 5:
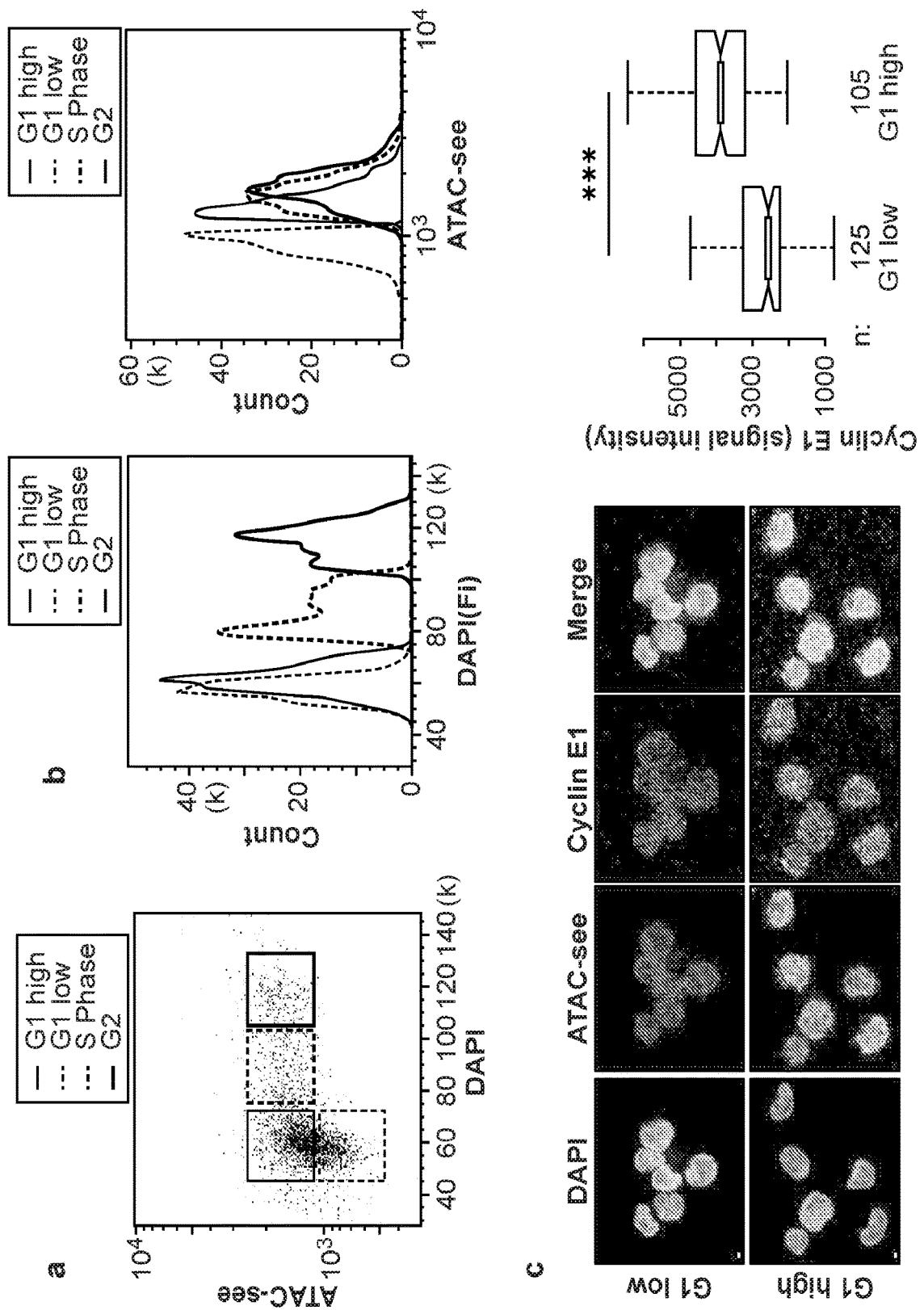
FIG. 5: ATAC-see reveals cell cycle specific genome accessibility. Panel a, Flow cytometry with ATAC-see. Dot plot of signal intensity in dual staining for DAPI and ATAC-see of GM12878 cells, and results showed four groups of cells: G1 low, G1 high, S phase and G2. Panel b, Quantitation of DAPI (left) and ATAC-see (right) signals from different groups. Panel c, Cyclin E1 staining in ATAC-see sorted G1 high and G1 low group: left panel is signal intensity measurement (n=cell number); right panel is representative images from confocal microscopy. Scale bar=2 µm. Panel d, Heatmap shows cluster of different ATAC-seq accessible regions between G1 high and G1 low group (FD>2, FDR<0.05), and each group has one replicate. Panel e, The volcano plot represents genome-wide comparisons of accessible regions in G1 high vs. G1 low. Panel f, The density bars represent the distribution of the more accessible regions in G1 high and G1 low group across the transcription starting sites (TSS). The more accessible regions in two groups were color-coded.
Figure 5:
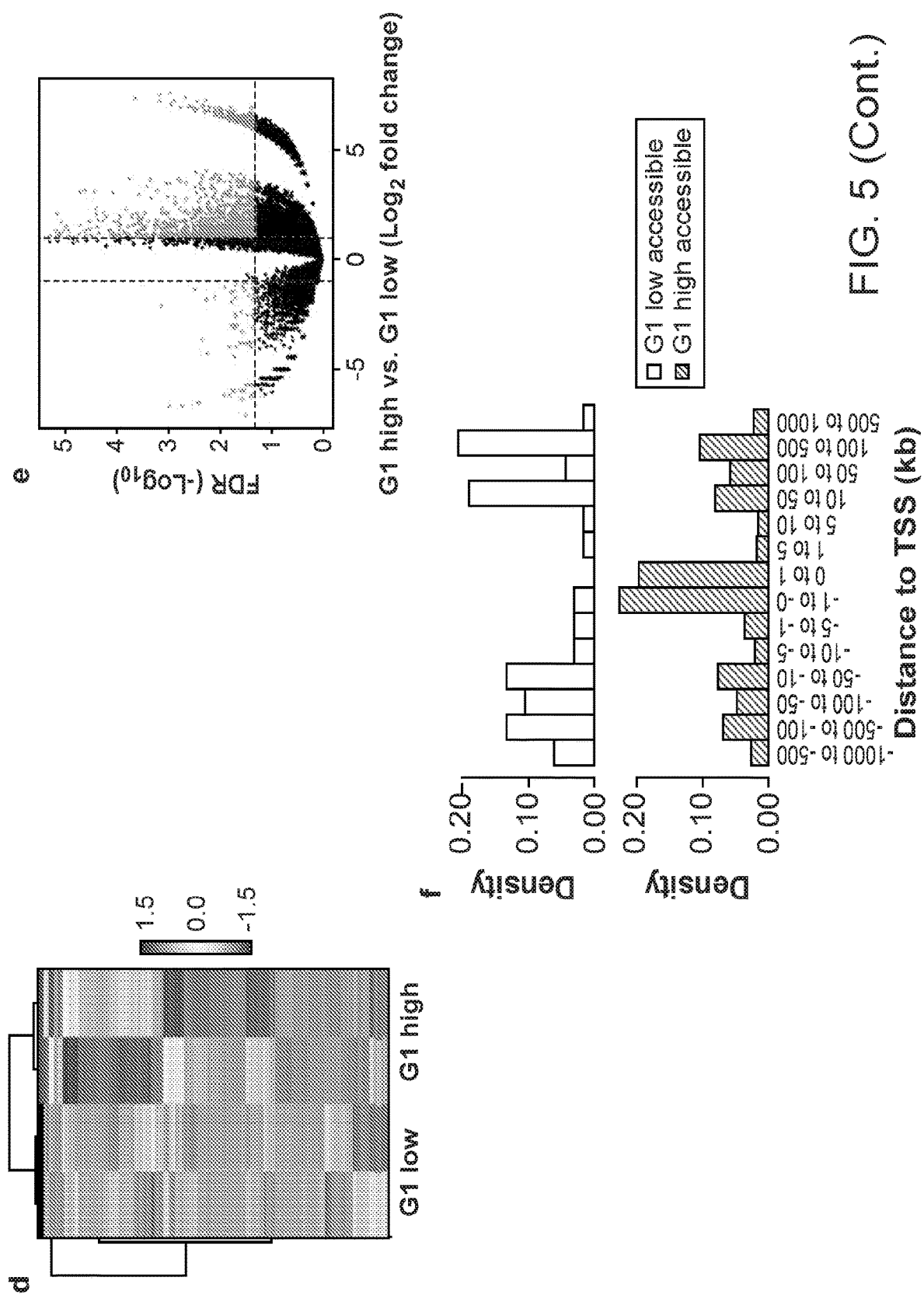

Finally, ATAC-see was integrated with flow cytometry to explore quantitative cell counting and prospective cell sorting as a function of chromatin accessibility. A central question in epigenetics is how chromatin organization is disassembled and reassembled during the cell cycle[28]. ATAC-see and DAPI staining of DNA content were employed for fluorescence activated cell sorting (FACS) in human B-cell line GM12878. It was found four groups of cells—G1 low, G1 high, S phase and G2—with approximately half of the cells in G1 (2N DNA content) having a lower level of ATAC-see signal (FIG. 5 panels a, b). It was hypothesized that the G1 low cells are in early G1, as the chromatin structure starts to de-condense after maximal chromosome compaction during mitosis. Staining with Cyclin E1, a late G1/S transition marker[29], clearly showed that low vs. high DNA accessible cells in G1 correspond to early vs. late G1 (FIG. 5 panel c, p<0.001).

ATAC-seq further showed that the two G1 populations have differential DNA accessibility profiles compared to each other and to S and G2 phase cells. Focusing on G1 low vs. G1 high cells, 96 loci that have relatively higher accessibility (fold change (FC)>2, FDR<0.05) in G1 low cells were identified; conversely, 2067 loci have increased DNA accessibility (FC>2, FDR<0.05) in G1 high compared to G1 low cells (FIG. 5 panels d-e). Notably, a majority (59.3%) of the more accessible loci in G1 low cells are enhancers, and the largest category (57.4%) of the more accessible loci in G1 high cells are promoters (FIG. 5 panel f). These results raise the possibility that certain enhancers become accessible first in early G1, followed by many promoters in mid to late G1. Gene Ontology analysis shows the accessible elements in G1 high cells are enriched for genes with histone acetyltransferase activity, histone modification, gene transcription, nuclear body and other biological process, consistent with stepwise re-building of chromatin and nuclear architecture from early G1 to late G1 stage after cell division. In a separate application, it was found that ATAC-see of mouse bone marrow cells can distinguish several myeloid cell populations by flow cytometry, separating common myeloid progenitor (CMP) cells, granulocyte-monocyte progenitor (GMP) cells and neutrophils. These FACS data are confirmed by confocal imaging. Collectively, these experiments demonstrate the feasibility of ATAC-see and flow cytometry to dissect cell population heterogeneity and enhance cell state-specific signals that may be otherwise averaged out in the bulk population.

REFERENCES

1. Bickmore et al. *Cell* 152, 1270-1284 (2013).
2. Misteli et al. *Proceedings of the National Academy of Sciences of the United States of America* 106, 6885-6886 (2009).
3. Buenrostro et al. *Nature methods* 10, 1213-1218 (2013).
4. Fullwood, M. J. et al. An oestrogen-receptor-alpha-bound human chromatin interactome. *Nature* 462, 58-64 (2009).
5. Barski, A. et al. *Cell* 129, 823-837 (2007).
6. Lieberman-Aiden et al. *Science* 326, 289-293 (2009).
7. Markaki et al. *BioEssays: news and reviews in molecular, cellular and developmental biology* 34, 412-426 (2012).
8. Deng et al. *Proceedings of the National Academy of Sciences of the United States of America* 112, 11870-11875 (2015).
9. Amini et al. *Nature genetics* 46, 1343-1349 (2014).
10. Buenostro et al. *Nature* 523, 486-U264 (2015).
11. Cusanovich et al. *Science* 348, 910-914 (2015).
12. Chaumeil et al. *Gene Dev* 20, 2223-2237 (2006).
13. Giorgetti et al. *Nature*, Epub ahead of Print (2016).
14. Gibcus et al. *Molecular cell* 49, 773-782 (2013).
15. Buys et al. *Human genetics* 52, 133-138 (1979).
16. Lanctot et al. *Nature reviews. Genetics* 8, 104-115 (2007).
17. Luckheeram et al. *Clin Dev Immunol* (2012).
18. Kolaczkowska et al. *Nat Rev Immunol* 13, 159-175 (2013).
19. Qu et al. *Cell systems* 1, 51-61 (2015).
20. Guelen et al. *Nature* 453, 948-951 (2008).
21. Amendola et al. *EMBO reports* 16, 610-617 (2015).
22. Solovei et al. *Cell* 137, 356-368 (2009).
23. Brinkmann et al. *Science* 303, 1532-1535 (2004).
24. Kolaczkowska et al. *Nat Rev Immunol* 13, 159-175 (2013).
25. Li et al. *J Exp Med* 207, 1853-1862 (2010).
26. Lewis et al. *Nat Chem Biol* 11, 189-+(2015).
27. Christophorou et al. *Nature* 507, 104-108 (2014).
28. Hinde et al. *Biophysical journal* 102, 691-697 (2012).
29. Aleem et al. *Nature cell biology* 7, 831-836 (2005).

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications those skilled in the art will recognize that its usefulness is not limited thereto and that the present invention can be beneficially utilized in any number of environments and implementations where it is desirable to examine analytes. Accordingly, the claims set forth below should be construed in view of the full breadth and spirit of the invention as disclosed herein.

What is claimed is:

1. A method for detecting accessible chromatin, comprising:
   a) providing a population of cells on a planar surface and a transposase complex comprising a transposase bound to at least one nucleic acid adapter comprising a recognition sequence for said transposase and an optically detectable label;
   b) contacting said population of cells with said transposase complex under conditions suitable for transposition, thereby inserting said at least one nucleic acid adapter at an accessible region of chromatin in said population of cells;
   c) staining said population of cells with a mitochondrial marker;
   d) imaging said population of cells to detect said optically detectable label and said mitochondrial marker, and using said mitochondrial marker to exclude a mitochondrial contribution to an analysis of said population of cells;
   e) lysing said population of cells; and
   f) performing a sequencing reaction to determine said accessible region of chromatin.

2. The method of claim 1, wherein said optically detectable label is a fluorophore.

3. The method of claim 1, further comprising identifying regulatory DNA, a transcription factor binding site, or a nucleosome binding site in said accessible region of chromatin.

4. The method of claim 1, further comprising mapping positions of sites that said at least one nucleic acid adapter inserts into said accessible region of chromatin.

5. The method of claim 1, wherein said population of cells is a population of fixed cells.

6. The method of claim 1, wherein said at least one nucleic acid adapter comprises (i) a first nucleic acid adapter comprising a first oligonucleotide comprising the nucleotide sequence of SEQ ID NO:1 or a nucleotide sequence having at least 95% identity to the sequence of SEQ ID NO:1 and a second oligonucleotide comprising the nucleotide sequence of SEQ ID NO: 2 or a nucleotide sequence having at least 95% identity to the sequence of SEQ ID NO: 2, and (ii) a second nucleic acid adapter comprising a first oligonucleotide comprising the nucleic acid sequence of SEQ ID NO: 1 or a nucleotide sequence having at least 95% identity to the sequence of SEQ ID NO: 1 and a second oligonucleotide comprising the nucleotide sequence of SEQ ID NO: 3 or a nucleotide sequence having at least 95% identity to the sequence of SEQ ID NO: 3.

7. The method of claim 1, wherein said transposase is a MuA transposase or a Tn transposase.

8. The method of claim 7, wherein said Tn transposase is a Tn5 transposase or a hyperactive Tn5 transposase.

9. The method of claim 1, wherein said population of cells is lysed on said planar surface.

10. The method of claim 1, further comprising staining said population of cells with one or more immunofluorescent markers and wherein (d) further comprises imaging said population of cells to detect said one or more immunofluorescent markers.

11. The method of claim 1, wherein said mitochondrial marker is an anti-mitochondria antibody and wherein imaging said population of cells to detect said mitochondrial marker comprises detecting said anti-mitochondria antibody using immunofluorescence.

12. The method of claim 1, further comprising staining said population of cells with DAPI, wherein (d) further comprises imaging said population of cells to detect said DAPI.

13. The method of claim 12, further comprising using DAPI image data to identify and segment cell nuclei of said population of cells.

14. The method of claim 11, wherein excluding said mitochondrial contribution to said analysis of said population of cells comprises using a mitochondrial mask generated by Gaussian filtering and applying an intensity threshold to a immunofluorescent signal detected from said mitochondrial marker.

15. The method of claim 5, further comprising, prior to (e) adding a reverse crosslink solution.

16. The method of claim 1, wherein said population of cells is 500 to 50,000 cells.

17. The method of claim 10, wherein said one or more immunofluorescent markers comprise an anti-lamin B1 antibody, an anti-H3K9 me3 antibody, an anti-H3K4 me3 antibody, an anti-H3K27 me3 antibody, an anti-H3K27 acetylation antibody, or an anti-RNA polymerase II antibody.

18. The method of claim 17, wherein said one or more immunofluorescent markers are a primary antibody and wherein detecting said one or more immunofluorescent markers comprises binding a fluorescently labeled secondary antibody to said primary antibody.

19. The method of claim 11, wherein said anti-mitochondria antibody is a primary antibody and wherein detecting said anti-mitochondria antibody using immunofluorescence comprises binding a fluorescently labeled secondary antibody to said anti-mitochondria antibody.

20. The method of claim 13, wherein segmenting cell nuclei of said population of cells comprises using a Gaussian filter on said DAPI image data and applying an intensity threshold to generate nuclear outlines of said cell nuclei.

* * * * *

SEQUENCE LISTING

<160> NUMBER OF SEQ ID NOS: 3

<210> SEQ ID NO 1
<211> LENGTH: 19
<212> TYPE: DNA
<213> ORGANISM: artificial sequence

```
<220> FEATURE:
<223> OTHER INFORMATION: synthetic oligonucleotides

<400> SEQUENCE: 1
ctgtctctta tacacatct                                                19

<210> SEQ ID NO 2
<211> LENGTH: 33
<212> TYPE: DNA
<213> ORGANISM: artificial sequence
<220> FEATURE:
<223> OTHER INFORMATION: synthetic oligonucleotide

<400> SEQUENCE: 2
tcgtcggcag cgtcagatgt gtataagaga cag                                33

<210> SEQ ID NO 3
<211> LENGTH: 34
<212> TYPE: DNA
<213> ORGANISM: artificial sequence
<220> FEATURE:
<223> OTHER INFORMATION: synthetic oligonucleotide

<400> SEQUENCE: 3
gtctcgtggg ctcggagatg tgtataagag acag                               34
```